United States Patent
Kibbe et al.

(10) Patent No.: US 9,517,275 B2
(45) Date of Patent: Dec. 13, 2016

(54) TARGETED THERAPY FOR THE PREVENTION OF RESTENOSIS IN THE CARDIOVASCULAR SYSTEM

(71) Applicant: Northwestern University, Evanston, IL (US)

(72) Inventors: Melina R. Kibbe, Chicago, IL (US); Samuel I. Stupp, Chicago, IL (US); Tyson J. Moyer, Chicago, IL (US); Edward Moreira Bahnson, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/502,252

(22) Filed: Sep. 30, 2014

(65) Prior Publication Data

US 2015/0151002 A1 Jun. 4, 2015

Related U.S. Application Data

(60) Provisional application No. 61/884,582, filed on Sep. 30, 2013.

(51) Int. Cl.
*A61K 38/00* (2006.01)
*A61K 47/00* (2006.01)
*A61K 47/48* (2006.01)
*A61K 33/00* (2006.01)
*C07K 14/78* (2006.01)

(52) U.S. Cl.
CPC ......... *A61K 47/48346* (2013.01); *A61K 33/00* (2013.01); *C07K 14/78* (2013.01); *A61K 38/00* (2013.01)

(58) Field of Classification Search
CPC .. A61K 33/00; A61K 38/00; A61K 47/48346; C07K 14/78
See application file for complete search history.

(56) References Cited

U.S. PATENT DOCUMENTS

| | | | |
|---|---|---|---|
| 6,063,407 A | 5/2000 | Zapol et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,452,649 B2 | 11/2008 | Magome et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,080,262 B2 | 12/2011 | Lee et al. | |
| 8,114,834 B2 | 2/2012 | Hsu et al. | |
| 8,114,835 B2 | 2/2012 | Mata et al. | |
| 8,124,583 B2 | 2/2012 | Stupp et al. | |
| 8,138,140 B2 | 3/2012 | Stupp et al. | |
| 8,450,271 B2 | 5/2013 | Shah et al. | |
| 8,512,693 B2 | 8/2013 | Capito et al. | |
| 8,748,569 B2 * | 6/2014 | Stupp ..................... | A61K 38/00 530/300 |
| 2007/0088435 A1 * | 4/2007 | Stamler ................ | A61K 31/785 623/11.11 |
| 2008/0299657 A1 | 12/2008 | Stupp et al. | |
| 2010/0119573 A1 * | 5/2010 | Jun .................. | A61K 47/48276 424/423 |
| 2010/0203142 A1 | 8/2010 | Zhang et al. | |
| 2012/0294902 A1 * | 11/2012 | Stupp ..................... | A61K 38/00 424/400 |
| 2013/0101628 A1 * | 4/2013 | Webber ................ | C07K 14/001 424/400 |
| 2013/0203647 A1 | 8/2013 | Uchegbu et al. | |

FOREIGN PATENT DOCUMENTS

WO WO 2013/134360 9/2013
WO WO 2015/048747 4/2015

OTHER PUBLICATIONS

Alef et al., Nitric oxide and nitrite-based therapeuitc opportunities in intimal hyperplasia. Nitric Oxide. 2012;26:285-294.
Barbato et al., Nitric oxide and arterial disease. J Vasc Surg. 2004;40:187-193.
Chan et al., In vivo prevention of arterial restenosis with paclitaxel-encapsulated targeted lipid—polymeric nanoparticles. Proceedings of the National Academy of Sciences. 2011;108:19347-19352.
Chan et al., Spatiotemporal controlled delivery of nanoparticles to injured vasculature. Proceedings of the National Academy of Sciences. 2010;107:2213-2218.
Choi et al., Mechanism of active targeting in solid tumors with transferrin-containing gold nanoparticles. Proceedings of the National Academy of Sciences. 2010;107:1235-1240.
Clowes et al., Kinetics of cellular proliferation after arterial injury. I. Smooth muscle growth in the absence of endothelium. Lab Invest. Sep. 1983;49(3):327-33.
Clowes et al., Kinetics of cellular proliferation after arterial injury. II. Inhibition of smooth muscle growth by heparin. Lab Invest. Jun. 1985;52(6):611-6.
Clowes et al., Kinetics of cellular proliferation after arterial injury. III. Endothelial and smooth muscle growth in chronically denuded vessels. Lab Invest. Mar. 1986;54(3):295-303.
Cui et al., Self-assembly of giant peptide nanobelts. Nano Lett. 2009;9:945-951.
Cui et al., Self-assembly of peptide amphiphiles: From molecules to nanostructures to biomaterials. Biopolymers. 2010;94:1-18.
Davies et al., Reduction of experimental vein graft intimal hyperplasia and preservation of nitric oxide-mediated relaxation by the nitric oxide precursor I-arginine. Surgery. 1994;116:557-568.

(Continued)

*Primary Examiner* — Marcela M Cordero Garcia
(74) *Attorney, Agent, or Firm* — Casimir Jones SC; David Staple

(57) ABSTRACT

Provided herein are compositions and methods for targeted drug delivery to prevent restenosis in the cardiovascular system. In particular, provided herein are nanoscale delivery vehicles for drugs that prevent proliferation and neointimal hyperplasia.

21 Claims, 19 Drawing Sheets

(56) References Cited

OTHER PUBLICATIONS

Davis et al., Evidence of rnai in humans from systemically administered sirna via targeted nanoparticles. Nature. 2010;464:1067-1070.
Decuzzi et al., Intravascular delivery of particulate systems: Does geometry really matter? Pharm Res. 2008;26:235-243.
Doshi et al., Flow and adhesion of drug carriers in blood vessels depend on their shape: A study using model synthetic microvascular networks. Journal of Controlled Release. 2010;146:196-200.
Farokhzad et al., Nanoparticle-aptamer bioconjugates a new approach for targeting prostate cancer cells. Cancer Research. 2004;64:7668-7672.
Fleser et al., Nitric oxide-releasing biopolymers inhibit thrombus formation in a sheep model of arteriovenous bridge grafts. J Vasc Surg. 2004;40:803-811.
Fulton et al., Local effects of nitric oxide supplementation and suppression in the development of intimal hyperplasia in experimental vein grafts. European journal of vascular and endovascular surgery : the official journal of the European Society for Vascular Surgery. 1998;15:279-289.
Furchgott et al., The obligatory role of endothelial cells in the relaxation of arterial smooth muscle by acetylcholine. Nature. 1980;288:373-376.
Garg et al., Nitric oxide-generating vasodilators and 8—bromocyclic guanosine monophosphate inhibit mitogenesis and proliferation of cultured rat vascular smooth muscle cells. J Clin Invest. May 1989;83(5):1774-7.
Geng et al., Shape effects of filaments versus spherical particles in flow and drug delivery. Nature Nanotechnology. 2007;2:249-255.
Guo et al., Mechanisms of vascular preservation by a novel no donor following rat carotid artery intimal injury. The American journal of physiology. 1995;269:H1122-1131.
Hartgerink et al., Self-assembly and mineralization of peptide—amphiphile nanofibers. Science. 2001;294:1684-1688.
Hartgerink et al., Peptide-amphiphile nanofibers: A versatile scoffold for the preparation of self-assembling materials. PNAS. 2002;99:5133-5138.
Havelka et al., Nitric oxide delivery a permeable balloon catheter inhibits neointimal growth after arterial injury. Journal of Surgical Research. Mar. 2013;180(1):35-42.
Hrabie et al., Chemistry of the nitric oxide-releasing diazeniumdiolate ("nitrosohydroxylamine") functional group and its oxygen-substituted derivatives. Chemical reviews. 2002;102:1135-1154.
Hrkach et al., Preclinical development and clinical translation of a psma-targeted docetaxel nanoparticle with a differentiated pharmacological profile. Science Translational Medicine. 2012;4:12839-12839.
Huang et al., Biological synthesis of tooth enamel instructed by an artificial matrix. Biomaterials. 2010;31:9202-11.
Israelavhvili, Intermolecular and Surface Forces. 2nd Edition, Academic Press, London, 1991, TOC only, 9 pages.
Jiang et al., The internal structure of self-assembled peptide amphiphiles nanofibers. Soft Matter. 2007;3:454-462.
Kapadia et al., Nitric oxide and nanotechnology: A novel approach to inhibit neointimal hyperplasia. Journal of vascular surgery. 2008;47:173-182.
Keefer, Progress toward clinical application of the nitric oxide-releasing diazeniumdiolates. Annual review of pharmacology and toxicology. 2003;43:585-607.
Kornowski et al., In-Stent Restenosis: Contributions of Inflammatory Responses and Arterial Injury to Neointimal Hyperplasia. JACC. 1998;31:224-30.
Kubes et al., Nitric oxide: An endogenous modulator of leukocyte adhesion. Proceedings of the National Academy of Sciences. 1991;88:4651-4655.
Lablanche et al., Effect of the direct nitric oxide donors linsidomine and molsidomine on angiographic restenosis after coronary balloon angioplasty. The accord study. Angioplastic coronaire corvasal diltiazem. Circulation. 1997;95:83-89.
Lebleu et al., Structure and function of basement membranes. Experimental Biology and Medicine. 2007;232:1121-1129.
Lee et al., Chronic inhalation of nitric oxide inhibits neointimal formation after balloon-induced arterial injury. Circulation research. 1996;78:337-342.
Marks et al., Inhibition of neointimal proliferation in rabbits after vascular injury by a single treatment with a protein adduct of nitric oxide. The Journal of clinical investigation. 1995;96:2630-2638.
Mata et al., Bone Regeneration Mediated by Biomimetic Mineralization of Nanofiber Matrix. Biomaterials. 2010;31:6004-12.
Mathews et al., Biological activity of s-nitrosothiols: The role of nitric oxide. Journal of Pharmacology and Experimental Therapeutics. 1993;267:1529-1537.
Matson et al., A peptide-based material for therapeutic carbon monoxide delivery. Soft matter. 2012;8:2689-2692.
Matson et al., Self-assembling peptide scaffolds for regenerative medicine. Chemical Communications. 2012;48:26-33.
McNamara et al., L—arginine inhibits balloon catheter-induced intimal hyperplasia. Biochemical and biophysical research communications. 1993;193:291-296.
Muraoka et al., Light-triggered bioactivity in three dimensions. Angew. Chem. Int. Ed. 2009;48:5946-5949.
Napoli et al., Effects of nitric oxide-releasing aspirin versus aspirin on restenosis in hypercholesterolemic mice. Proceedings of the National Academy of Sciences of the United States of America. 2001;98:2860-2864.
Paramonov et al., Self-Assembly of Peptide-Amphiphile Nanofibers: The Roles of Hydrogen Bonding and Amphiphilic Packing. J Am Chem Soc2006;128:7291-7298.
Pashuck et al., Tuning Supramolecular Rigidity of Peptide Fibers through Molecular Structure. J Am Chem Soc. 2010;132:6041-46.
Pashuck et al., Direct observation of morphological tranformation from twisted ribbons into helical ribbons. J. Am. Chem. Soc. 2010;132:8819-8821.
Pearce et al., Beneficial effect of a short-acting no donor for the prevention of neointimal hyperplasia. Free radical biology & medicine. 2008;44:73- 81.
Rassaf et al., Evidence for in vivo transport of bioactive nitric oxide in human plasma. J Clin Invest. 2002;109:1241-48.
Schwarzacher et al., Local intramural delivery of l—arginine enhances nitric oxide generation and inhibits lesion formation after balloon angioplasty. Circulation. 1997;95:1863-1869.
Selcuk et al., Endovascular Treatment of Persistent Epistaxis due to Pseudoaneurysm Formation of the Ophthalmic Artery Secondary to Nasogastric Tube. Cardiovasc Intervent Radiol. 2005;28:242-45.
Shah et al., Supramolecular design of self-assembling nanofibers for cartilage regeneration. PNAS. 2010;107:3293-3298.
Shears et al., Efficient inhibition of intimal hyperplasia by adenovirus-mediated inducible nitric oxide synthase gene transfer to rats and pigs in vivo. Journal of the American College of Surgeons. 1998;187:295-306.
Shuvaev et al., Endothelial Targeting of Antibody-Decorated Polymeric Filomicelles. ACS Nano. 2011;5:6991-6999.
Soukasene et al., Antitumor activity of peptide amphiphile nanofiber-encapsulated camptothecin. ACS Nano. 2011;5:9113-9121.
Stamler, S-nitrosothiols and the bioregulatory actions of nitrogen oxides through reactions with thiol groups. Current topics in microbiology and immunology. 1995;196:19-36.
Toft et al., Coassembled cytotoxic and pegylated peptide amphiphiles form filamentous nanostructures with potent antitumor activity in models of breast cancer. ACS Nano. 2012;6:7956-7965.
Vance et al., The design of polyvalent scaffolds for targeted delivery. Advanced Drug Delivery Reviews. 2009;61:931-939.
Varenne et al., Local adenovirus-mediated transfer of human endothelial nitric.

(56) References Cited

OTHER PUBLICATIONS

Vavra et al., Insights into the effect of nitric oxide and its metabolites nitrite and nitrate at inhibiting neointimal hyperplasia. Nitric oxide : biology and chemistry / official journal of the Nitric Oxide Society. 2011;25:22-30.

Von Der Leyen et al., Gene therapy inhibiting neointimal vascular lesion: In vivo transfer of endothelial cell nitric oxide synthase gene. Proceedings of the National Academy of Sciences of the United States of America. 1995;92:1137-1141.

Webber et al., Supramolecular nanostructures that mimic VEGF as a strategy fo ischemic tissue repair. PNAS. 2011;108:13438-443.

Ziche et al., Nitric oxide mediates angiogenesis in vivo and endothelial cell growth and migration in vitro promoted by substance p. J. Clin. Invest. 1994;94:2036.

International Search Report and Written Opinion for PCT/US2014/058316, mailed Jan. 29, 2015, 19 pages.

\* cited by examiner

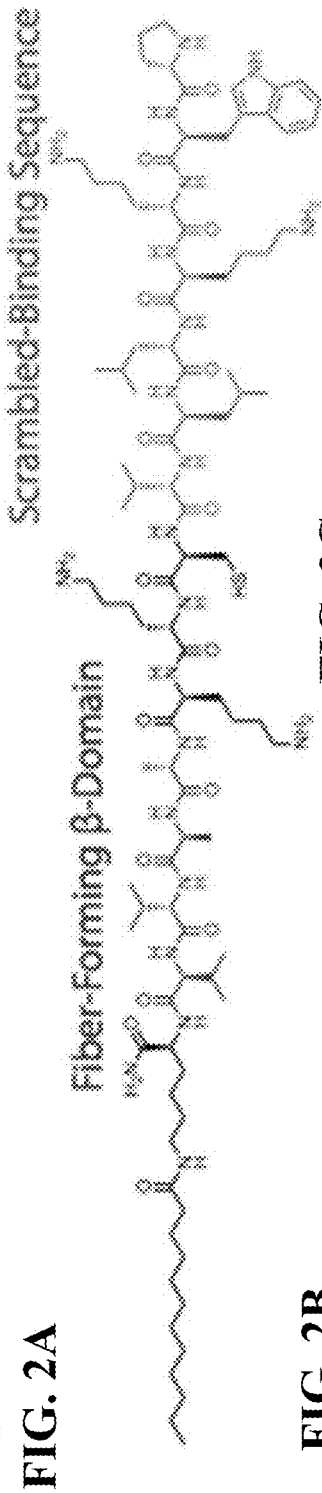
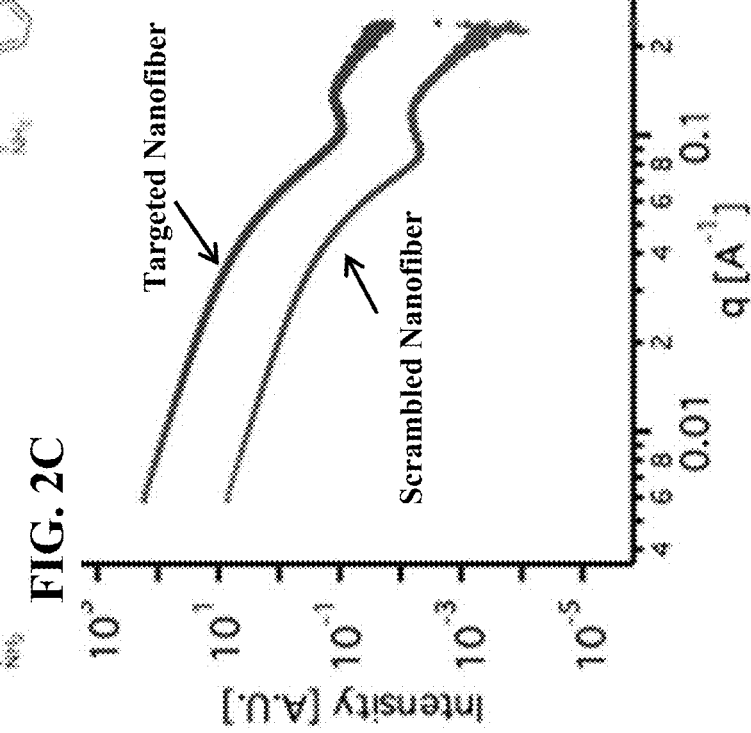
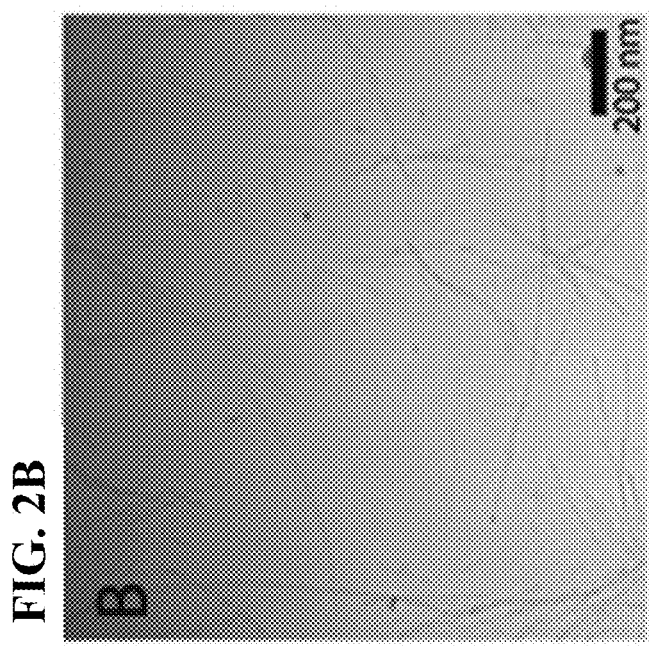
FIG. 2A
FIG. 2B
FIG. 2C

FIG. 5A
FIG. 5B
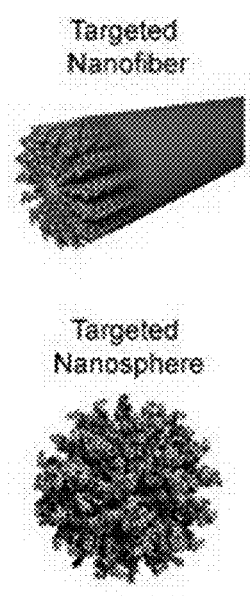
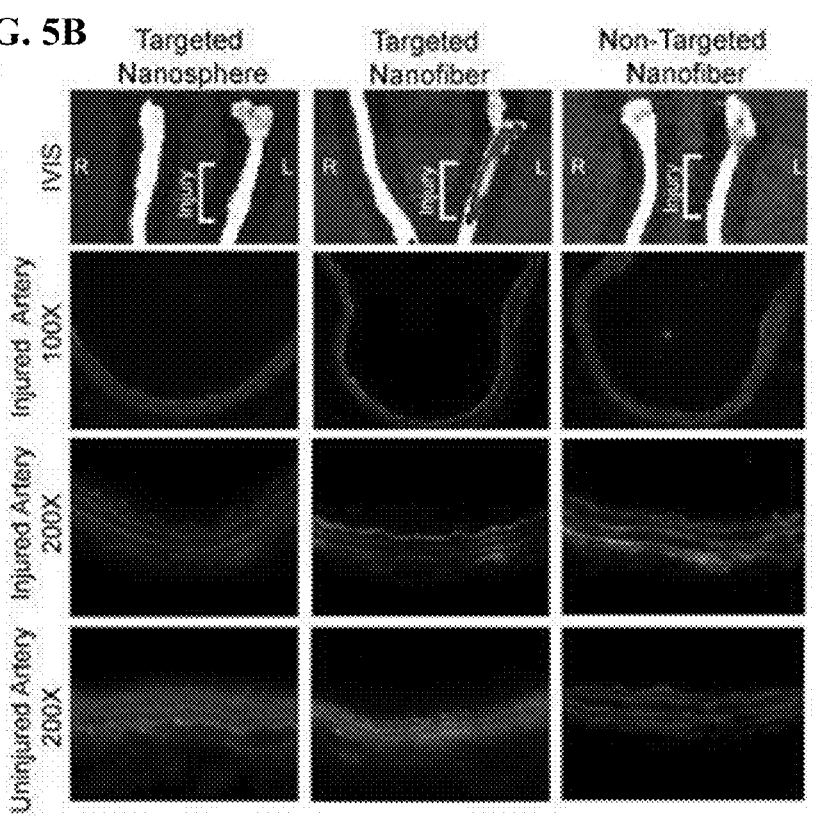

FIG. 5C  FIG. 5D
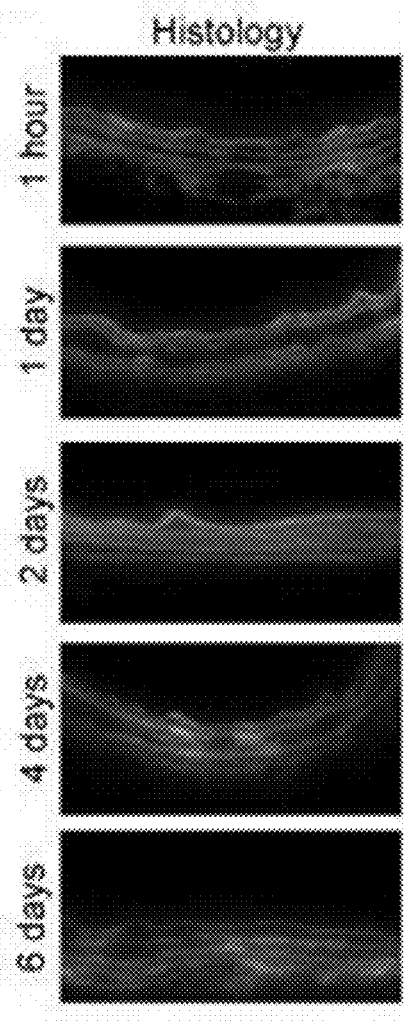
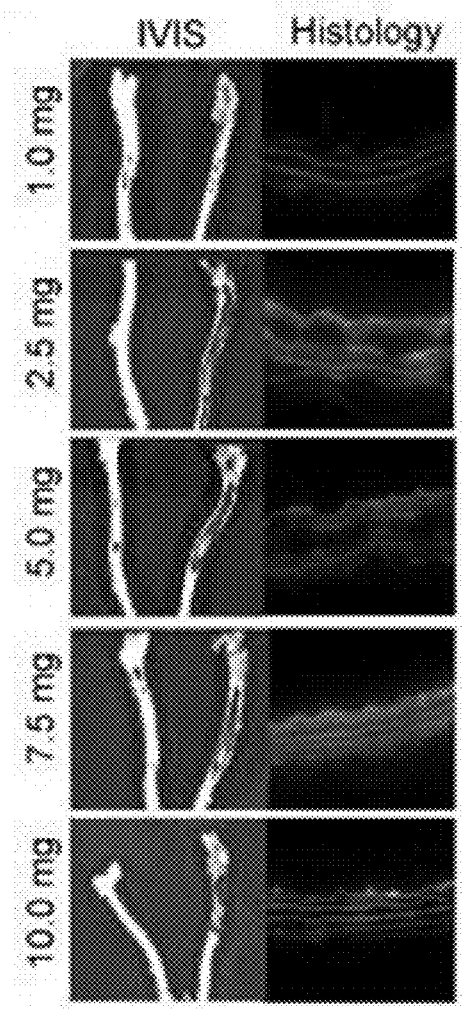

SEQUENCE LISTING

```
<160> NUMBER OF SEQ ID NOS: 3

<210> SEQ ID NO 1
<211> LENGTH: 15
<212> TYPE: PRT
<213> ORGANISM: Artificial sequence
<220> FEATURE:
<223> OTHER INFORMATION: Synthetic peptide

<400> SEQUENCE: 1

Lys Leu Val Trp Leu Pro Lys Cys Lys Lys Ala Ala Val Val Lys
1               5                   10                  15

<210> SEQ ID NO 2
<211> LENGTH: 7
<212> TYPE: PRT
<213> ORGANISM: Artificial sequence
<220> FEATURE:
<223> OTHER INFORMATION: Synthetic peptide

<400> SEQUENCE: 2

Lys Leu Val Trp Leu Pro Lys
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

Ala Ala Val Val
1
```

TARGETED THERAPY FOR THE PREVENTION OF RESTENOSIS IN THE CARDIOVASCULAR SYSTEM

CROSS REFERENCE TO RELATED APPLICATIONS

The present application claims the benefit of U.S. Provisional Patent Application Ser. No. 61/884,582, filed Sep. 30, 2013, which is incorporated by reference in its entirety.

FIELD

Provided herein are compositions and methods for targeted drug delivery to prevent restenosis in the cardiovascular system. In particular, provided herein are nanoscale delivery vehicles for drugs that prevent proliferation and neointimal hyperplasia.

BACKGROUND

Biocompatable nanoscale drug carriers incorporating targeting information have the potential to provide substantial improvement of drug delivery methods with high efficacy and minimal toxicity. Nanostructures can combine polyvalent display of small molecules (Hrkach, J., et al. Science Translational Medicine, Vol. 4 128ra139-128ra139 (2012); herein incorporated by reference in its entirety), aptamers (Farokhzad, O. C., et al. Cancer Research, Vol. 64 7668-7672 (AACR, 2004); herein incorporated by reference in its entirety), antibodies (Qian, X., et al. Nat Biotechnol, Vol. 26 83-90 (2007); herein incorporated by reference in its entirety), and proteins (Davis, M. E., et al. Nature, Vol. 464 1067-1070 (2010); Choi et al. Proceedings of the National Academy of Sciences, Vol. 107 1235-1240 (2010); herein incorporated by reference in their entireties) on their surfaces designed to release drugs at a targeted site (Vance et al. Advanced Drug Delivery Reviews, Vol. 61 931-939 (2009); herein incorporated by reference in its entirety). Most work in this area has focused on cancer therapies, with very few examples targeting cardiovascular pathologies (Chan, J. M., et al. Proceedings of the National Academy of Sciences, Vol. 107 2213-2218 (2010); herein incorporated by reference in its entirety). Specifically, cardiovascular interventions, such as bypass grafting, or angioplasty with and without stenting have limited durability due to eventual arterial reocclusion. This reocclusive process initiated at the site of intervention involves inflammatory processes, as well as cellular proliferation and migration, among other events (Kornowski, R., et al. Journal of the American College of Cardiology, Vol. 31 224-230 (1998); herein incorporated by reference in its entirety). Ultimately, this arterial injury response leads to what is known as neointimal hyperplasia, which narrows the lumen of the blood vessel. Developing a therapy to effectively prevent the formation of neointimal hyperplasia, while simultaneously promoting vascular healing, is a significant unmet clinical need.

The physiological gas nitric oxide (NO) has many vascular protective properties (Barbato, J. E. & Tzeng, E. Journal of Vascular Surgery, Vol. 40 187-193 (2004); Garg, U. C. & Hassid, A. J. Clin. Invest., Vol. 83 1774 (1989); Kubes et al. Proceedings of the National Academy of Sciences, Vol. 88 4651-4655 (1991); Dubey et al. J. Clin. Invest., Vol. 96 141 (1995); herein incorporated by reference in their entireties), including inhibition of the processes that lead to neointimal hyperplasia (Alef et al. Nitric Oxide, Vol. 26 285-294 (Elsevier Inc., 2012); herein incorporated by reference in its entirety). Furthermore, NO is known to promote the healing of the inner layer of the arterial wall populated by endothelial cells (Ziche, M., et al. J. Clin. Invest., Vol. 94 2036 (1994); herein incorporated by reference in its entirety). Systemic delivery of NO donors has limited clinical application due to toxicity and potential side effects (Keefer, L. K. Annual review of pharmacology and toxicology, Vol. 43 585-607 (2003); herein incorporated by reference in its entirety). Local delivery of NO has shown efficacy in vivo (Kapadia, M. R., et al. Journal of Vascular Surgery, Vol. 47 173-182 (2008); Fleser, P. S., et al. Journal of Vascular Surgery, Vol. 40 803-811 (2004); Selcuk, H., et al. Cardiovasc Intervent Radiol, Vol. 28 242-245 (2005); herein incorporated by reference in its entirety), but is not clinically translatable because it requires invasive procedures for delivery or is limited to single dose application. NO is a challenging molecule to deliver owing to its short half-life, rapid metabolism, and reactivity (Rassaf, T., et al. J. Clin. Invest., Vol. 109 1241-1248 (2002); herein incorporated by reference in its entirety). Systemically delivered NO-based approaches have been limited in their clinical translation due to non-clinically tenable delivery schemes (e.g., extended exposure to NO gas), systemic side effects (e.g., bleeding and hypotension from the large doses of NO delivered from NO donors to achieve efficacy), or safety concerns (e.g, gene therapy).

Peptide amphiphiles (Hartgerink et al. P Natl Acad Sci USA 99, 5133 (2002); Hartgerink et al. Science 294, 1684 (2001); herein incorporated by reference in their entireties) (PAs) are a class of self-assembling molecules that are composed of a hydrophobic segment conjugated to a sequence of amino acids. PAs can form long, high aspect ratio cylindrical filaments in water and have been studied for a range of applications in regenerative medicine (Mata et al., Biomaterials 31, 6004 (2010); Shah et al., P Natl Acad Sci USA 107, 3293 (2010); Huang et al. Biomaterials 31, 9202 (2010); Webber et al., P Natl Acad Sci USA 108, 13438 (2011); herein incorporated by reference in their entireties). PA bioactivity is derived from presentation of peptide sequences on the surface of self-assembled nanostructures that form in solution. The rheological properties of these materials can be tuned by concentration and peptide sequence (Pashuck et al. Journal of the American Chemical Society 132, 6041 (2010); herein incorporated by reference in its entirety).

SUMMARY

Provided herein are compositions and methods for targeted drug delivery to prevent restenosis in the cardiovascular system. In particular, the provided herein are nanoscale delivery vehicles for drugs that prevent proliferation and neointimal hyperplasia.

In some embodiments, provided herein are peptide amphiphiles comprising: (a) a hydrophobic non-peptidic segment; (b) a β-sheet-forming peptide segment; (c) a charged peptide segment; (d) a targeting moiety; and (e) a therapeutic agent. In some embodiments, the hydrophobic non-peptidic segment is covalently attached to the N-terminus of the β-sheet-forming peptide segment; wherein the C-terminus of the β-sheet-forming peptide segment is covalently attached to the N-terminus of the charged peptide segment; and wherein the C-terminus of the charged peptide segment is covalently attached to the N-terminus of the targeting moiety. In some embodiments, the hydrophobic non-peptidic segment comprises an acyl chain. In some embodiments, the acyl chain comprises $C_6$-$C_{24}$ (e.g., $C_6 \ldots C_8 \ldots C_{10} \ldots C_{12} \ldots C_{14} \ldots C_{16} \ldots C_{18} \ldots C_{20} \ldots C_{22} \ldots C_{24}$). In some embodiments, the acyl chain comprises lauric acid. In some embodiments, the β-sheet-forming peptide segment comprises AAVV (SEQ ID NO: 3). In some embodiments, the charged peptide segment comprises a plurality of Lys (K), Arg (R), Glu (E) and/or Asp (D) residues. In some embodiments, the charged peptide segment comprises 2-7 amino acids in length with 50% or more amino acids selected from Lys (K), Arg (R), Glu (E) and/or Asp (D) residues. In some embodiments, the charged peptide segment comprises KK. In some embodiments, the targeting moiety comprises a binding sequence for a target protein. In some embodiments, the target protein is a cardiovascularly expressed protein. In some embodiments, the target protein is collagen IV. In some embodiments, the binding sequence comprises a 6 amino acid segment with at least 50% sequence identity with KLVWLPK (SEQ ID NO: 2). In some embodiments, the binding sequence comprises KLVWLPK (SEQ ID NO: 2). In some embodiments, the therapeutic agent is covalently linked to the peptide amphiphile. In some embodiments, the therapeutic agent is nitric oxide (NO). In some embodiments, the NO is covalently linked to the peptide amphiphile as a nitroso group. In some embodiments, the nitroso group is attached via nitrosylation of a cysteine residue. In some embodiments, the peptide amphiphile comprises a peptide portion with at least 50% sequence identity with KLVWLPKCK$_2$A$_2$V$_2$K (SEQ ID NO: 1) and a (CH$_2$)$_{12}$ tail. In some embodiments, peptide amphiphile comprises KLVWLPKCK$_2$A$_2$V$_2$K—(CH$_2$)$_{12}$ (SEQ ID NO: 1). In some embodiments, the peptide amphiphile comprises an S-nitrosylated cysteine residue.

In some embodiments, provided herein are self-assembled nanofibers formed of the peptide amphiphiles described above (or elsewhere herein). In some embodiments, the nanofiber has a diameter of less than 200 nm (e.g., <150 nm, <100 nm, <50 nm). In some embodiments, the nanofiber has a diameter of 10-200 nm (e.g., 20-180 nm, 50-200 nm, 30-150 nm, or other ranges less than 200 nm and greater than 10 nm). In some embodiments, the nanofiber has a length of at least 1 μm. In some embodiments, the nanofiber has a length of at least 500 nm to 50 μm (e.g., >500 nm, >1 μm, >2 μm, >5 μm, >10 μm, <50 μm, <40 μm, <30 μm, <20 μm, etc.).

In some embodiments, provided herein are methods of treating or preventing cardiovascular restenosis comprising administering to a subject a self-assembled nanofiber described above (or elsewhere herein).

In some embodiments, provided herein are methods of treating or preventing cardiovascular restenosis comprising administering to a subject a therapeutic agent linked to a binding sequence for a vascularly-expressed protein. In some embodiments, the therapeutic agent is selected from the list consisting of nitric oxide (NO), acetylsalicylic acid, rapamycin, and paclitaxel. In some embodiments, the therapeutic agent comprises NO. In some embodiments, the vascularly-expressed protein is selected from the list consisting of elastin, laminin, fibroinectin, collagen I, collagen III, collagen IV, and collagen V. In some embodiments, the vascularly-expressed protein is collagen IV. In some embodiments, the binding sequence comprises a 6 amino acid segment with at least 50% sequence identity with KLVWLPK (SEQ ID NO: 2). In some embodiments, the binding sequence comprises 3-6 amino acids with 100% sequence identity to all or a portion of KLVWLPK (SEQ ID NO: 2). In some embodiments, the binding sequence comprises KLVWLPK (SEQ ID NO: 2). In some embodiments, the therapeutic agent and the binding sequence are covalently linked as portions of a peptide amphiphile. In some embodiments, the peptide amphiphile further comprises a β-sheet forming peptide segment, a non-peptidic hydrophobic segment, and a charged peptide segment. In some embodiments, a plurality of peptide amphiphiles is self-assembled into a nanofiber. In some embodiments, the nanofiber is administered to a subject and the nanofiber localizes in the cardiovascular system. In some embodiments, the nanofiber is administered systemically. In some embodiments, the nanofiber is administered locally. In some embodiments, the nanofiber localizes in the vasculature. In some embodiments, the nanofiber localizes at a site of vascular intervention. In some embodiments, the subject has undergone a cardiovascular intervention. In some embodiments, the cardiovascular intervention is selected from bypass grafting, angioplasty, and stenting.

In some embodiments, provided herein are methods of treating or preventing cardiovascular restenosis in a subject who has undergone a cardiovascular intervention comprising administering to the subject a self-assembled nanofiber comprising a vascular targeting moiety and a therapeutic agent that prevents proliferation and neointimal hyperplasia. In some embodiments, the nanofiber is a complex of peptide amphiphiles comprising: (a) a hydrophobic non-peptidic segment; (b) a β-sheet-forming peptide segment; (c) a charged peptide segment; and (d) a vascular targeting moiety; and (e) a therapeutic agent that prevents proliferation and neointimal hyperplasia. In some embodiments, the vascular targeting moiety comprises a collagen IV binding peptide. In some embodiments, the therapeutic agent that prevents proliferation and neointimal hyperplasia comprises nitric oxide (NO). In some embodiments, the NO is covalently linked to the peptide amphiphiles. In some embodiments, the NO is encapsulated by the nanofiber.

In some embodiments, provided herein are methods of treating or preventing a disease or condition in a subject suffering from said disease or condition comprising administering to the subject a self-assembled nanofiber comprising a targeting moiety and a therapeutic agent, wherein the targeting moiety localizes the nanofiber to the site of the cause of the disease of condition and the therapeutic agent treats or prevents the disease or condition.

BRIEF DESCRIPTION OF THE DRAWINGS

FIGS. 2A-C. Non-targeted collagen peptide amphiphile (PA). (A) Chemical structure of the non-targeted PA with a scrambled targeting sequence. (B) Cryogenic transmission electron microscopy (Cryo-TEM) of non-targeted nanofibers. (C) Small angle x-ray scattering (SAXS) shows comparable morphologies for the non-targeted and targeted nanofibers.

FIGS. 5A-D. In vivo targeting of targeted nanostructures. (A) Molecular graphics of the targeted nanofiber and targeted nanosphere. (B) Fluorescent image of gross injured and uninjured carotid arteries (top row) and arterial cross-sections of injured left carotid artery at 100× (2nd row), 200× (3rd row), and right uninjured carotid artery at 200× (4th row). (C) Cross-sectional fluorescence imaging of injured carotid arteries from animals injected with the targeted nanofiber (5.0 mg) over time. (D) Fluorescent images of gross and 200× cross-sections of uninjured and injured carotid arteries 1 hour after injection of the targeted nanofiber at various doses.

DEFINITIONS

Figure 1A:
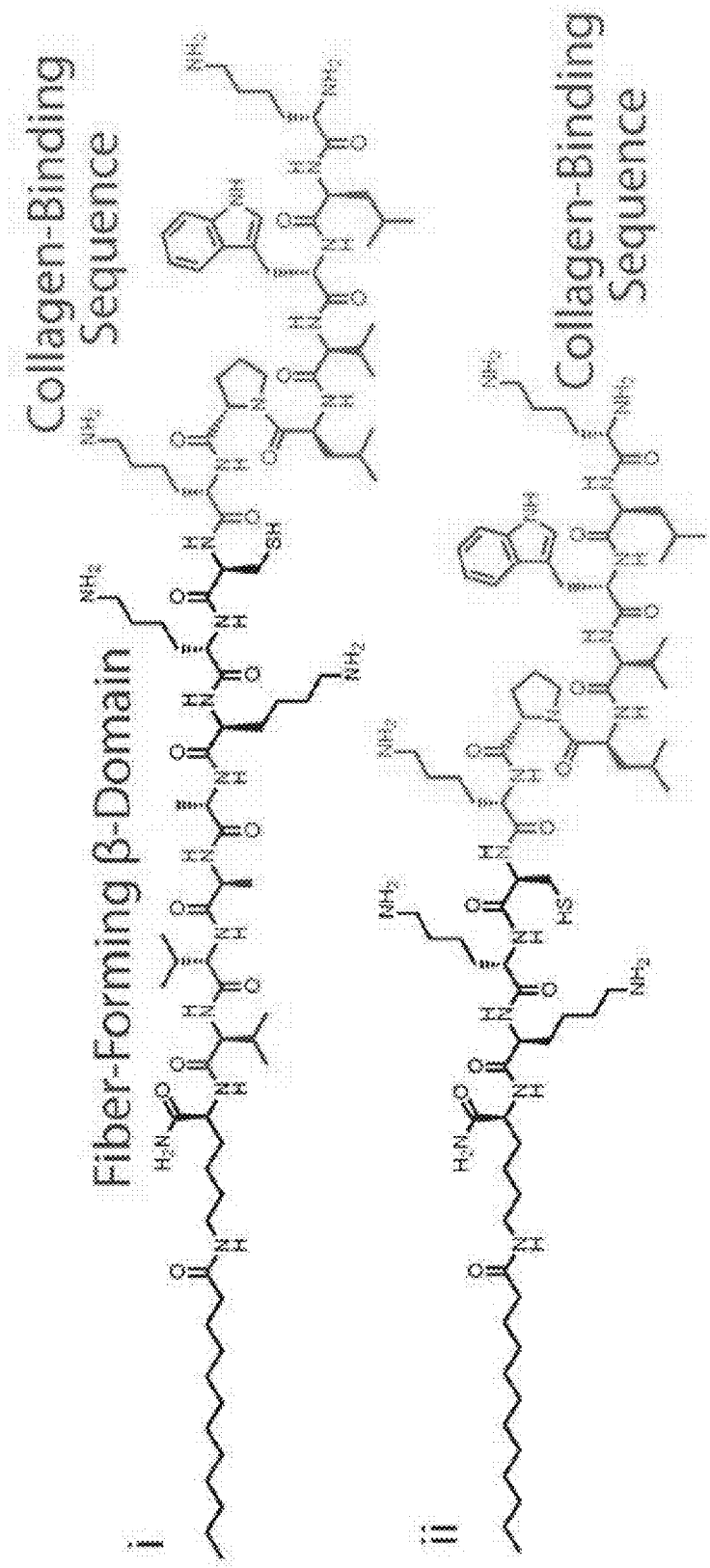
FIGS. 1A-E. Collagen-targeting peptide amphiphiles assemble into nanofiber and nanospheres in aqueous solutions. (A) Structures of the targeted nanofiber (i) and targeted nanosphere (ii). (B) Cryo-transmission electron microscopy (TEM) of the targeted nanofiber and (C) targeted nanosphere. (D) Small angle x-ray scattering (SAXS) of the targeted nanofiber and targeted nanosphere with fits for a polydisperse core-shell cylinder and core-shell sphere (red). (E) Differences in secondary structure shown by circular dichroism of the targeted nanofiber and targeted nanopshere.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "nanofiber" refers to an elongated or threadlike filament (e.g., having a significantly greater length dimension that width or diameter) with a diameter of less than 100 nanometers.

As used herein, the term "nanosphere" refers to an approximately spherical (e.g., a globular shape having approximately (<25% difference, <10% difference, <5% difference) the same diameters in the x, y, and z dimensions) with a diameter of less than 500 nanometers (e.g., <200 nm, <100 nm, etc.).

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and optionally a functional peptide segment. The peptide amphiphile may express a net charge at physiological pH, either a net positive or negative net charge, or may be zwitterionic (i.e., carrying both positive and negative charges). Certain peptide amphiphiles consist of or comprise four segments: (1) a hydrophobic, non-peptidic segment comprising an acyl group of six or more carbons, (2) a β-sheet-forming peptide segment; (3) a charged peptide segment, and (4) a targeting moiety (e.g., targeting peptide).

As used herein and in the appended claims, the term "lipophilic component" or "hydrophobic component" refers to the acyl moiety disposed on the N-terminus of the peptide amphiphile. This lipophilic segment may be herein and elsewhere referred to as the lipophilic or hydrophobic segment. The hydrophobic component should be of a sufficient length to provide amphiphilic behavior and micelle (or nanosphere or nanofiber) formation in water or another polar solvent system.

Accordingly, in the context of the embodiments described herein, the hydrophobic component preferably comprises a single, linear acyl chain of the formula: $C_{n-1}H_{2n-1}C(O)-$ where n=6-22. A particularly preferred single, linear acyl chain is the lipophilic group, palmitic acid. However, other small lipophilic groups may be used in place of the acyl chain.

As used herein, the term "structural peptide" or "beta-sheet forming peptide" refers to the intermediate amino acid sequence of the peptide amphiphile molecule between the hydrophobic segment and the charged peptide segment of the peptide amphiphile. This "structural peptide" or "beta-sheet forming peptide" is generally composed of three to ten amino acid residues with non-polar, uncharged side chains, selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety). In a preferred embodiment, the N-terminus of the structural peptide segment is covalently attached to the oxygen of the lipophilic segment and the C-terminus of the structural peptide segment is covalently attached to the N-terminus of the charged peptide segment.

As used herein, the term "charged peptide segment" refers to the intermediately disposed peptide sequence between the structural peptide segment or beta-sheet forming segment and the functional peptide. In some embodiments, the charged segment provides for solubility of the peptide amphiphile in an aqueous environment, and preferably at a delivery location within a cell, tissue, organ, or subject. The charged peptide segment contains two or more amino acid residues that have side chains that are ionized under physiological conditions, examples of which selected from the 20 naturally occurring amino acids include Lys (K), Arg (R), Glu (E) and/or Asp (D), along with other uncharged amino acid residues. Non-natural amino acid residues with ionizable side chains could be used, as will be evident to one ordinarily skilled in the art. There may be from about 2 to about 7 amino acids, and or about 3 or 4 amino acids in this segment. The charged peptide segment may include those amino acids and combinations thereof which provide this solubility and permit self-assembly and is not limited to polar amino acids such as E or K and combinations of these for modifying the solubility of the peptide amphiphile.

One or more Gly (G) residues may be added to the "charged peptide segment," intermediately disposed between the charged residues and the functional peptide segment (e.g., targeting peptide). While not wishing to be bound by theory, the inclusion of one or more Gly (G) residues appears to prevent salt-bridge formation between the Glu and the Lys amino acid side-chains by altering side-chain orientation of these residues relative to each other, improving solubility of the peptide in salt solutions of similar composition to extracellular fluid. In one embodiment, the charged peptide segments have the formula $(E)_x (G)_y$, wherein x is 2 to 6 and y is 1 to 6. In another embodiment, the charged peptide segment has 2 to 4 Glu (E) residues and 1 to 2 Gly (G) residues. In another aspect, the charged peptide segment has 2 Glu (E) residues and 1 Gly (G) residue. In yet another aspect of the invention, the charged peptide segment has 3 Glu (E) residues and 1 Gly (G) residue. In another embodiment, the charged peptide segment has 4 Glu (E) residues and 1 Gly (G) residue.

As used herein, the term "targeting peptide" refers to amino acid sequences which mediates the localization (or retention) of sequences, molecules, or supramolecular complexes associated therewith to a particular location or locations (e.g., sub-cellular location (e.g., organelle), an organ (e.g., heart), tissue (e.g., cardiovascular tissue), or localized with a receptor or binding partner for the targeting peptide). Peptide amphiphiles and structures (e.g., nanofibers) bearing targeting peptides have been reported to congregate in desired locations based on the identity and presence of the targeting peptide. A targeting peptide described in exemplary embodiments herein is the collagen-binding peptide. Such targeting peptides have been shown to delivery targeted nanofibers comprising such peptides to the site of arterial intervention.

DETAILED DESCRIPTION

Provided herein are compositions and methods for targeted drug delivery to prevent restenosis in the cardiovascular system. In particular, provided herein are nanoscale delivery vehicles for drugs that prevent proliferation and neointimal hyperplasia.

Provided herein are nanostructures for delivery of cardiovascular therapeutics (e.g., nitric oxide (NO)) that prevent occlusion at the site of intervention (e.g., arterial intervention). These nanoscale constructs are based on self-assembling biodegradable molecules known as peptide amphiphiles (PAs), and in some embodiments assemble as fibers or spherical nanostructures. In some embodiments, the delivery vehicles comprise a targeting moiety (e.g., collagen-binding peptide). Experiments conducted during development of embodiments described herein demonstrated that following systemic delivery targeted nanofibers were localized to the site of arterial intervention; however, targeted nanospheres of comparable diameter failed to bind. For example, S-nitrosylated targeted nanofibers were found to significantly reduce arterial narrowing two weeks following balloon angioplasty in a rat model. In some embodiments, supramolecular nanofibers integrating both therapeutic and targeting moieties provide treatment for vascular and other diseases.

In some embodiments, provided herein are supramolecular nanostructures (e.g., formed by self-assembly of a single molecule type) that targets the site of vascular injury and deliver therapeutic (e.g., NO). An exemplary molecular building block for the supramolecular nanostructures is a peptide amphiphile (PA) containing a peptide segment conjugated to an aliphatic tail. This broad family of molecules is in the creation, assembly, and/or manufacture of bioactive nanostructures for regenerative medicine and drug delivery (Cui, et al. Biopolymers, Vol. 94 1-18 (2010); Matson & Stupp. Chem. Commun, Vol. 48 26 (2011); Webber, M. J., et al. Proceedings of the National Academy of Sciences, Vol. 108 13438-13443 (2011); Matson, et al. Soft Matter, Vol. 8 6689 (2012); Soukasene, S., et al. ACS Nano, Vol. 5 9113-9121 (2011); herein incorporated by reference in their entireties). PAs self-assemble into nanostructures of various shapes, including spheres and fibers, by altering the peptide sequences (Muraoka et al. Angew. Chem. Int. Ed., Vol. 48 5946-5949 (2009); Cui et al. Nano Lett., Vol. 9 945-951 (2009); Paramonov et al. J. Am. Chem. Soc., Vol. 128 7291-7298 (2006); herein incorporated by reference in their entireties). This ability is attractive to vascular applications because a filamentous shape has been previously shown to extend circulation time and bind to the endothelium (Geng, Y., et al. Nature Nanotechnology, Vol. 2 249-255 (2007); Shuvaev, V. V., et al. ACS Nano, Vol. 5 6991-6999 (2011); herein incorporated by reference in their entireties). The peptide portion of a PA is also an ideal site to integrate various bioactive functions.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH$_2$, and —NH$_2$.

The lipophilic segment is typically incorporated at the N-terminus of the peptide after the last amino acid coupling, and is composed of a fatty acid or other acid that is linked to the N-terminal amino acid through an acyl bond. In aqueous solutions, PA molecules self-assemble (e.g., into cylindrical micelles (a.k.a nanofibers)) that bury the lipophilic segment in their core and display the functional peptide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl tail) segment of sufficient length (e.g., >3 carbons, >5 carbons, >7 carbons, >9 carbons, etc.) is covalently coupled to peptide segment (e.g., an ionic peptide having a preference for beta-strand conformations) to yield a peptide amphiphile molecule. In some embodiments, a plurality of such PAs will self-assemble in water (or aqueous solution) into a nanostrcuture (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostrcutural architecture. In various embodiments, hydrophobic segments pack in the center of the assembly with the peptide segments exposed to an aqueous or hydrophilic environment to form cylindrical nanostructures that resemble filaments. Such nanofilaments display the peptide regions on their exterior and have a hydrophobic core.

To induce self-assembly of an aqueous solution of peptide amphiphiles, the pH of the solution may be changed (raised or lowered) or multivalent ions, such as calcium, or charged polymers or other macromolecules may be added to the solution. Though not intending to be bound by theory, self-assembly is facilitated in the instant case by the neutralization or screening (reduction) of electrostatic repulsion between ionized side chains on the charged peptide segment.

In some embodiments, the hydrophobic segment is a non-peptide segment (e.g., alkyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, aromatic segments, pi-conjugated segments, etc.

In some embodiments, peptide amphiphiles comprise a targeting moiety. In particular embodiments, a targeting moiety is the C-terminal most segment of the PA. In some embodiments, the targeting moiety is attached to the C-terminal end of the charged segment. In some embodiments, the targeting moiety is exposed on the surface of a assembled PA structure (e.g., nanofiber). A targeting moiety is typically a peptide (e.g., targeting peptide), but is not limited thereto. For example, in some embodiments, a targeting moiety is a small molecule (e.g., the target for a receptor, a ligand for a protein, etc.). Examples described in detail herein utilize a peptide sequence that binds collagen-IV (the most abundant protein in the extracellular matrix of the vascular wall) as a targeting moiety. The presence of the collagen binding sequence directs the PA structures (e.g., nanofibers) to the vasculature, allowing them to localize at the site of vascular interventions (e.g., to isolate the therapeutic action at the desired site). Alternative targeting moieties for localization of PA structures to the vasculature include binders (e.g., binding peptide sequences) of elastin, laminin, fibroinectin, collagen I, collagen III, collagen V, etc. Further, targeting moieties may bind (and thereby direct PA structures to) proteins or other targets that are localized in other regions of the body, or even subcellular locations. Targeting moieties may direct PA structures (and therefore the therapeutics attached thereto or encapsulated therein) to specific organs, tissues, cell types, subcellular locations (e.g., organelles), pathogens (e.g., viruses, bacteria, etc.), diseases (e.g., to cancerous cells), etc. Targeting peptides and other moieties for achieving such localization are understood. As additional targeting moieties are discovered, they too may find use in embodiments described herein.

Suitable peptide amphiphiles, PA segments, PA nanostrcutures, and associated reagents and methods are described, for example in U.S. Pat. No. 8,512,693; U.S. Pat. No. 8,450,271; U.S. Pat. No. 8,138,140; U.S. Pat. No. 8,124,583; U.S. Pat. No. 8,114,835; U.S. Pat. No. 8,114,834; U.S. Pat. No. 8,080,262; U.S. Pat. No. 8,063,014; U.S. Pat. No. 7,851,445; U.S. Pat. No. 7,838,491; U.S. Pat. No. 7,745,708; U.S. Pat. No. 7,683,025; U.S. Pat. No. 7,554,021; U.S. Pat. No. 7,544,661; U.S. Pat. No. 7,534,761; U.S. Pat. No. 7,491,690; U.S. Pat. No. 7,452,679; U.S. Pat. No. 7,390,526; U.S. Pat. No. 7,371,719; U.S. Pat. No. 6,890,654; herein incorporated by reference in their entireties.

In certain embodiments, peptide amphiphiles further comprise a therapeutic group. In some embodiments, a therapeutic (e.g., a drug that prevents proliferation and neointimal hyperplasia (e.g., NO)) is covalently or non-covalently attached to PA. For example, a therapeutic is attached to a PA such that it is exposed on the surface of the assembled PA structure (e.g., nanofiber). In some embodiments, a therapeutic is covalently linked to the peptide portion of the PA. In some embodiments, any suitable chemistry known to those in the art is used for the covalent attachment (e.g., modification of a cysteine in the PA (e.g., S-nitrosylation)). In other embodiments, a therapeutic is attached to PA such that it is released (e.g., in a burst, over time, upon exposure to particular conditions, etc.) from the PA and/or assembled POA structure (e.g., nanofiber). In some embodiments, a therapeutic is not attached to the individual PAs, but is incorporated into or encapsulated within a PA surpamolecular structure. In such embodiments, the therapeutic is released from the structure at a desired rate and/or under desired conditions (e.g., physiological conditions, upon binding of the targeting moitety to a target, etc.).

Exemplary therapeutic groups include small molecules (e.g., NO), peptides, antibodies, nucleic acids (e.g., siRNA, antisense RNA, etc.), etc. Examples described in detail herein utilize nitric oxide as a therapeutic. In the examples, PAs were s-nitosylated (e.g., SNO groups added to the PAs). Upon degradation of the SNO groups, NO is released from the assembled PA structure (e.g., nanofiber). Therapeutic delivery of NO is not limited to s-nitrosylation of PAs. Further, embodiments are not limited to delivery of NO. Any therapeutic that can be delivered and localized to a desired site of action (e.g., by a targeting moiety) finds use in embodiments described herein. For example, drugs that prevent proliferation and neointimal hyperplasia may be delivered to sites of arterial intervention to reduce and/or prevent restenosis in the cardiovascular system. Exemplary drugs for such use include, but are not limited to: nitric oxide, acetylsalicylic acid, rapamycin, paclitaxel, etc.

The characteristics (e.g., shape, rigidity, hydrophilicity, etc.) of a PA supramolecular structure depend upon the identity of the components of a peptide amphiphile (e.g., lipophilic segment, charged segment, structural segment, functional segment, etc.). For example, nanofibers, nanosperes, intermediate shapes, and other supramolcular structures are achieved by adjusting the identity of the PA component parts. In examples provided herein, the fiber shape of the nanoscale delivery vehicle proved particularly conducive to cardiovascular applications, and exhibited significant and measurable advantage over, for example nanosphere delivery vehicles. In other embodiments, for example, when a different site of action is desired, other vehicle characteristics may be desirable. In some embodiments, provided herein are nanoscale delivery vehicles with tunable shapes to best suit the intended therapeutic delivery location. For example, nanofibers may be preferred over nanospheres for a particular delivery site (e.g., site of vascular intervention). Likewise, in some embodiments, a particular length to diameter ratio (or range of ratios) is particularly advantageous for a delivery location.

In certain embodiments, PAs and the nanofibers assembled therefrom comprise a targeting moiety configured to deliver the PA and/or nanofiber to a desired location within a cell, tissue, organ, body system, or subject (e.g., human, non-human primate, rodent, etc.). In some embodiments, a PA and/or nanofiber is also associated with (e.g., covalently or non-covalently) a therapeutic agent configured for action at the site to which the PA and/or nanofiber is localized. In exemplary embodiments described herein a collagen IV binding sequence that is part of a PA is used to localize a nanofiber covalently linked to nitric oxide to a site of intervention with the vasculature of a subject. Embodiments are not limited to such conditions (e.g., cardiovascular intervention or damage), targeting moieties (e.g., vascular targeting, collagen IV targeting, etc.), or therapeutics (e.g., NO). One of skill in the art will understand how to select and test combinations of therapeutic agents and targeting moieties for prevention and/or treatment of a variety of diseases and conditions. For example, a PA comprising tumor targeting peptides and linked to chemotherapeutics find use in the treatment of cancer. Likewise, PAs comprising peptides targeting clotting factors and linked to antithombic agents find use in the treatment or prevention of stroke and/or other cardiovascular conditions. Embodiments find use, for example, in the treatment or prevention of any disease or condition where systemic administration of a therapeutic, followed by localization to a treatment site, is desired.

EXPERIMENTAL

Experiments were conducted during development of embodiments described herein to synthesize a PA molecule in which the peptide segment includes a targeting sequence specific to sites of vascular injury and an S-nitrosylated amino acid to deliver NO. A peptide sequence that binds collagen-IV, the most abundant protein in the extracellular matrix of the vascular wall (LeBleu et al. Experimental Biology and Medicine, Vol. 232 1121-1129 (2007); herein incorporated by reference in its entirety), was used as a targeting moiety. This peptide sequence was derived using phage display in earlier studies (Chan, J. M., et al. Proceedings of the National Academy of Sciences, Vol. 108 19347-19352 (2011); Chan, J. M., et al. Proceedings of the National Academy of Sciences, Vol. 107 2213-2218 (2010); herein incorporated by reference in their entireties). The binding of both sphere- and fiber-forming PAs containing the same targeting sequence were investigated. Experiments conducted during development of embodiments described herein to demonstrate the successful targeting and therapeutic efficacy of a systemically delivered (e.g., NO-releasing) nanofiber in a small animal model.

Experiments conducted during development of embodiments described herein to (see Examples below) demonstrate that the integration of the nanostructure conformation (e.g., fibrous), target (e.g., collagen) binding sequence, and therapeutic (e.g., NO) provide a useful therapeutic effect. As detailed below, some other treatment groups failed to produce biologically relevant effects. These experiments demonstrate the utility of a systemically administered therapy (e.g., NO-based therapy) resulting in a local inhibitory effect (e.g., on neointimal hyperplasia). Experiments conducted during development of embodiments described herein to demonstrate the targeted delivery of NO to injured vasculature through a PA-based nanofiber. The shape of the nanostructure (e.g., fiber, sphere, etc.) was tunable by altering the amino acid sequence, different in vivo behaviors based on nanostructural shape were observed.

Example 1

Reagents and Methods

PA synthesis. The collagen-targeting PAs and peptides were synthesized using standard Fmoc solid-phase synthesis conditions. Coupling reactions included Fmoc-amino acids (4 equiv), HBTU (3.95 equiv) and diisopropylethylamine (DIEA) (6 equiv) in dimethylformamide (DMF). For the aliphatic tail of collagen-targeting PA (KLVWLPKCK2A2V2K(C12)) (SEQ ID NO: 1), lauric acid was attached to the ϵ-amine of a lysine, which was deprotected by selective removal of the 4-methyltrityl group (Mtt) using 2% trifluoroacetic acid (TFA)+5% triisopropylsilane (TIPS) in $CH_2Cl_2$. Cleavage was performed using a TFA/TIPS/$H_2O$/2,2'-(Ethylenedioxy)diethanethiol mixture (90:2.5:2.5:5).

Purification by preparative-scale high performance liquid chromatography (HPLC) was carried out on a Varian Prostar 210 HPLC system, eluting with 2% acetonitrile (ACN) to 100% ACN in water on a Phenomenex C18 Gemini NX column (150×30 mm) with 5 μm pore size and 110 Å particle size. 0.1% trifluoroacetic acid was added to both mobile phases to aid PA solubility during purification. Product-containing fractions were confirmed by ESI mass spectrometry (Agilent 6510 Q-TOF LC/MS), combined, and lyophilized after removing ACN by rotary evaporation. Purity was assessed by LC/MS.

Fluorescent labeling of the collagen-targeting PA was achieved by reacting AlexaFluor 546-maleimide with the cysteine in phosphate-buffered saline (PBS) (pH 7.4). Unreacted dye was removed by dialysis overnight in a 4 k MWCO membrane. Both fluorescently labeled PA and unlabeled PA were dissolved in hexafluoroisopropanol (HFIP), an organic solvent known to disrupt hydrogen bonds, and mixed together for at least 15 minutes. Samples were lyophilized to dryness to form a powder. After lyophilization in HFIP, samples were dissolved in water, aliquoted, and lyophilized again. The final percentage of fluorescently labeled PA was 1.8 mol % relative to total PA concentration.

S-Nitrosylation of PAs was achieved performed using slightly modified methods: 1 mM PA was dissolved in acidic solution (pH 3) with 1 eq. $NaNO_2$ and 50 μM DTPA for 1 hour, protected from light. The SNO PA was then lyophilized and stored at −20 C. For materials characterization, in vitro, and in vivo experiments, SNO PA powder was resuspended in PBS.

Materials Characterization.

Cryogenic transmission electron microscopy (cryo-TEM) specimens were prepared using an FEI Vitrobot by blotting in 95% humidity and subsequently plunging lacey carbon grids into liquid ethane. Images were taken for cryo-TEM using a JEOL 1230 transmission electron microscope operating at 100 keV equipped with a Gatan camera. For the targeted and scrambled nanofibers, the samples were dissolved at 250 uM in PBS prior to plunging, while the targeted nanosphere sample was dissolved at a higher concentration of 5 mM. The difference in concentrations was used to ensure visualization of the spheres during imaging. Samples were aged for 1-2 hours prior to plunging.

Small angle X-ray scattering (SAXS) experiments were performed at the Advanced Photon Source, Argonne National Laboratory. The X-ray energy (15 keV) was selected using a double-crystal monochromator with a 30 mm offset. Samples were dissolved at a concentration of 5 mM in PBS and placed in 1.5 mm quartz capillary tubes. The typical incident X-ray flux on the sample was ~$1 \times 10^{12}$ photons/s with a 0.2×0.3 $mm^2$ collimator, and samples were exposed for 4 s. The 1D scattering profiles were obtained by azimuthal integration of the 2D patterns, with scattering from the capillaries and PBS buffer subtracted as background. Scattering profiles were then plotted on a relative scale as a function of the scattering vector $q=(4\pi/\lambda) \sin(\theta/2)$, where θ is the scattering angle.

Circular dichroism was performed on a Zeiss spectrophotometer. PAs were dissolved at 500 uM in a mild (5 mM) phosphate buffer, and placed on 0.05 cm plates. Measurements were done with three accumulations at a speed of 50 nm/min. Critical aggregation concentrations (CACs) were determined by measuring maximum emission wavelength of Nile red. Nile red, dissolved in ethanol, was added to solutions of PAs or peptides for a final Nile Red concentration of 250 nM. The final concentration of ethanol was kept to a minimum (<0.5%) to prevent disruption of the assemblies. Fluorescence was measured using a NanologHJ Fluorometer.

NO Measurements and Release.

Lyophilized SNO PA powder was resuspended in $H_2O$, 0.1% formic acid for LC/MS analysis, described in further detail in the supporting information. Absorption measurements of the SNO bond formation were done on using a 96 well M5 plate reader, in triplicate. SNO decomposition was followed monitoring the SNO bond spectrophotometrically at 368 nm. NO release was assayed using the Apollo free radical analyzer equipped with a ISO-NOPF100 NO electrode (World Precision Instruments, Fl). An aliquot of the nanofiber or the SNO-nanofiber (5 μM) was added to a vial containing 10 ml of PBS with or without Ascorbate (50 μM) and Cupper (1 μM).

Cell Proliferation Assay.

VSMC proliferation was assayed by the $^3$H-Thymidine incorporation assay in the presence of the nanofiber or the SNO-nanofiber. VSMC were seeded onto 96-well plates at a density of 3,500 cells/well. Cells were allowed to adhere overnight followed by serum starvation for 24 h to synchronize the culture. Cells were treated with the nanofiber in the presence of 5 μCi $^3$H-Thymidine. After 24 h the DNA was precipitated with 5% trichloroacetic acid at 4° C. The plate was thoroughly washed and the DNA resuspended in 0.3 M NaOH, transferred to scintillation vials, and the radioactivity counted.

Animal Surgery.

All animal procedures were performed in accordance with the Guide for the Care and Use of Laboratory Animals (National Institutes of Health Publication 85-23, 1996) and approved by the Northwestern University Animal Care and Use Committee. Adult male Sprague-Dawley rats weighing 350 to 400 g underwent carotid artery balloon injury as previously described.[34] After injury, arteriotomy was ligated and Heparin 50 U/kg was injected through the tail vein of the animal. After the Heparin circulated for 10 minutes, PA dissolved in 1 mL of HBBS was injected via tail vein injection into the animal. Restoration of blood flow to the carotid artery injured site was resumed after the PA was completely injected and the neck incision was closed. For the binding studies 5 mg of the nanofiber or the nanosphere was injected. Rats were euthanized at 1 hour, 1, 2, 4, 6 days post-injection to assess binding of the PA. For the dosage study, different concentrations of the targeted nanofiber were used (1-10 mg) and carotids were explanted 1 h post injection.

Clearance Study.

Adult male Sprague-Dawley rats weighing 350 to 400 g underwent midline neck incision with exposure of internal jugular vein. Targeted nanofiber 2.5 mg was dissolved in 1.0 mL of HBBS and injected within the internal jugular vein using 25 G needle. After complete injection, needle was withdrawn, pressure held at the injection site for 1 minute and the neck incision was closed. Rats were euthanized at 10, 15, 30, 60 min, 4, 16 hours, 4 and 6 days post injection and viscera (liver, lung, kidney and spleen) were harvested.

Effect of Targeted Nanofibers on NIH.

Adult male Sprague-Dawley rats weighing 350 to 400 g underwent carotid artery balloon injury as previously described.[34] After injury, arteriotomy was ligated and Heparin 50 U/kg was injected through the tail vein of the animal. After the Heparin circulated for 10 minutes, targeted or non-targeted nanofibers with or without NO (5 mg) dissolved in 1 mL of HBBS injected via tail vein injection. Restoration of blood flow to the carotid artery injured site was resumed after the peptide ampiphile was completely injected and the neck incision was closed. Rats were euthanized at 14 days (n=6 per group).

Tissue Processing.

Carotid arteries and viscera were harvested after in-situ perfusion-fixation with PBS (250 mL) and placed in 2% paraformaldehyde overnight.

Morphometric Analysis.

Carotid arteries harvested at 14 days were examined histologically for evidence of neointimal hyperplasia using routine hematoxylin and eosin staining. Digital images were collected with light microscopy using an Olympus BHT microscope (Melville, N.Y.) with ×10 objective. Ten evenly spaced sections through each injured carotid artery were morphometrically analyzed. Lumen area, intimal area (I), medial area (M), and intimal/media ratio (arbitrary units) was obtained using ImageJ software (National Institutes of Health, Bethesda, Md.). Percent occlusion was calculated by the following calculation:

[(Lumen area/(Lumen+Intimal area))*100].

Fluorescent Imaging.

Carotid arteries harvested at respective time points and underwent fluorescent imaging. Digital images were acquired using a Zeiss LSM-510 microscope (Hallbergmoos, Germany) at ×40 using HE Cy3 filter (Zeiss filter #43) Ex: 550-575 Em: 605-670 nm.

Example 2

Effect of β-Domain Region on PA Supramolecular Assemblies

Figure 1B:
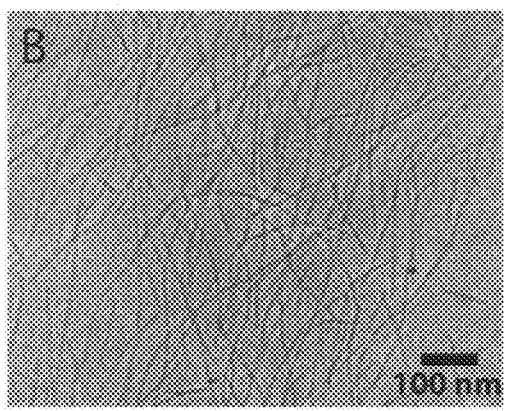
Figure 1C:
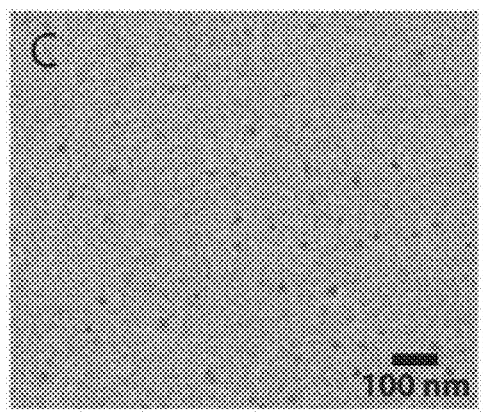
Figure 1D:
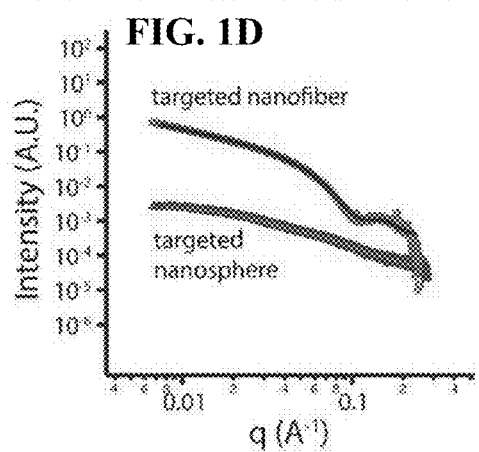

Two PAs were synthesized to test the effects of nanostructure on in vivo targeting. Both PAs contained the same collagen-binding peptide sequence (Chan, J. M., et al. Proceedings of the National Academy of Sciences, Vol. 107 2213-2218 (2010); herein incorporated by reference in its entirety) and an aliphatic tail, but one contained in addition the β-sheet forming domain AAVV to promote nanofiber formation (See FIG. 1A) (Jiang et al. Soft Matter, Vol. 3 454 (2007); herein incorporated by reference in its entirety). Cryo-TEM experiments revealed that the presence of the AAVV domain in one of the molecules was effective at inducing self-assembly into nanofibers, while its absence resulted in nanosphere formation (FIG. 1B). Based on cryo-TEM, the PA without a β-sheet forming region appeared to form spherical nano structures, roughly 10 nm in diameter (FIG. 1C). This structural difference was confirmed by synchrotron small-angle x-ray scattering (SAXS). Slopes of −1 and 0 in the low-q region of the scattering curve were observed for nanofibers and nanospheres, respectively. Further verification of the structural difference was obtained using a polydisperse core-shell fit for the nanofiber PA yielding a cylinder with an average diameter of 6 nm, which effectively corresponds to molecular dimensions (FIG. 1D). For the nanosphere system, a polydisperse core-shell model yielded a sphere with an average diameter of 10 nm (Tyson to add core/shell length discussion). Additionally, a control peptide of the binding peptide alone (KLWVLPKC) did not display any evidence of self-assembly by SAXS. These results demonstrate that the β-domain region is necessary for the formation of a one-dimensional fibrous assembly, while a PA with only a targeting sequence and an aliphatic tail is driven primarily by hydrophobic collapse to form spheres. A nanofiber containing a scrambled version of the collagen-binding sequence was synthesized. This PA also showed fiber formation by both cryo-TEM and SAXS (FIG. 2).

Figure 1E:
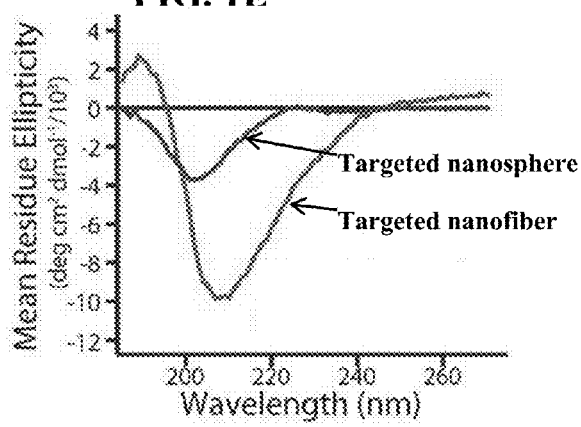
Figure 3:
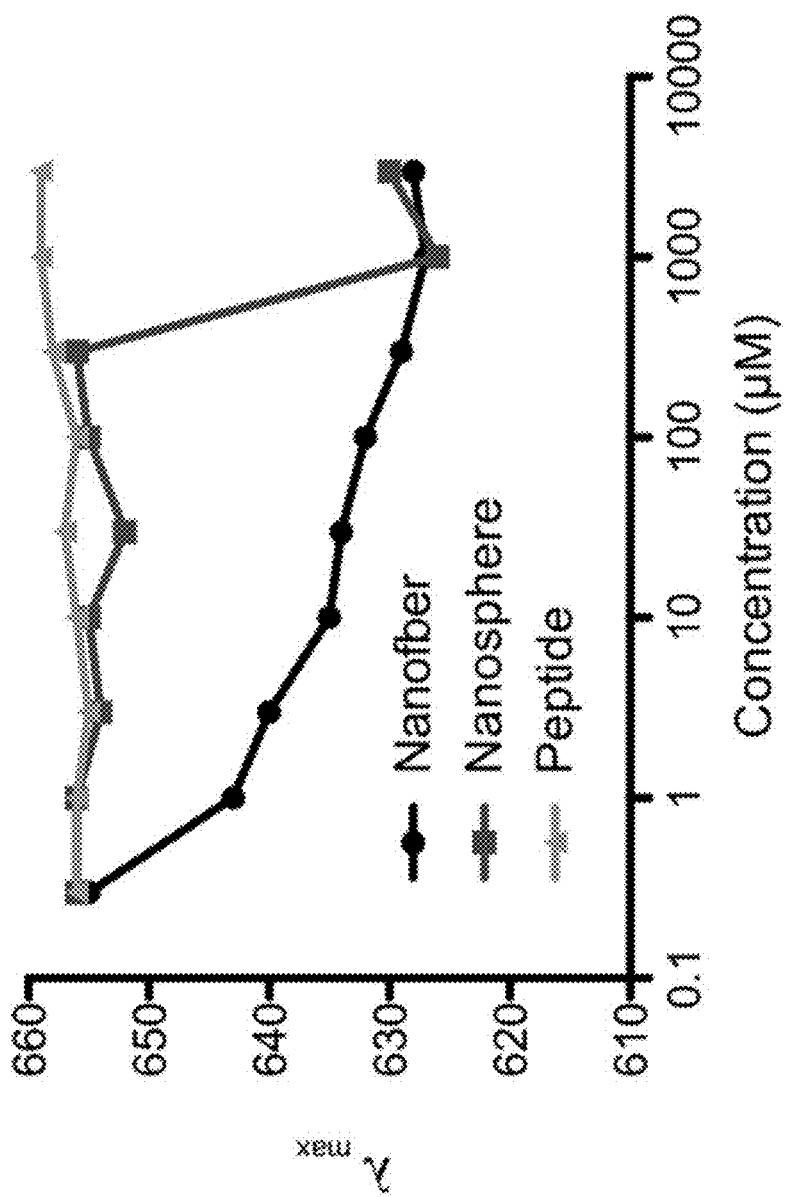
FIG. 3. Non-targeted collagen peptide amphiphile (PA). (A) Chemical structure of the non-targeted PA with a scrambled targeting sequence. (B) Cryogenic transmission electron microscopy (Cryo-TEM) of non-targeted nanofibers. (C) Small angle x-ray scattering (SAXS) shows comparable morphologies for the non-targeted and targeted nanofibers.

The inclusion of the β-domain region has a substantial effect on intermolecular packing and peptide secondary structure. Circular dichroism results showed more β-sheet character for the targeted nanofiber when compared to the targeted nanosphere, which displayed instead a random coil conformation (FIG. 1E). Critical aggregation concentrations (CAC) were measured for the sphere and fiber PAs using the maximum fluorescence emission of the hydrophobic dye Nile Red. A low CAC was observed for the targeted nanofiber (<300 nM), while the targeted sphere had a much higher CAC, at approximately 1 mM (FIG. 3). The combination of increased hydrophobicity and hydrogen bonding produced assemblies for the targeted nanofiber at much lower concentrations relative to the targeted sphere. These results indicate that, in addition to the observed effects of molecular structure on nanostructure morphology, the β-sheet region adds stability to the structures by remaining assembled at lower concentrations.

Example 3

In Vivo Binding of Targeted Nanostructures

Figure 4:
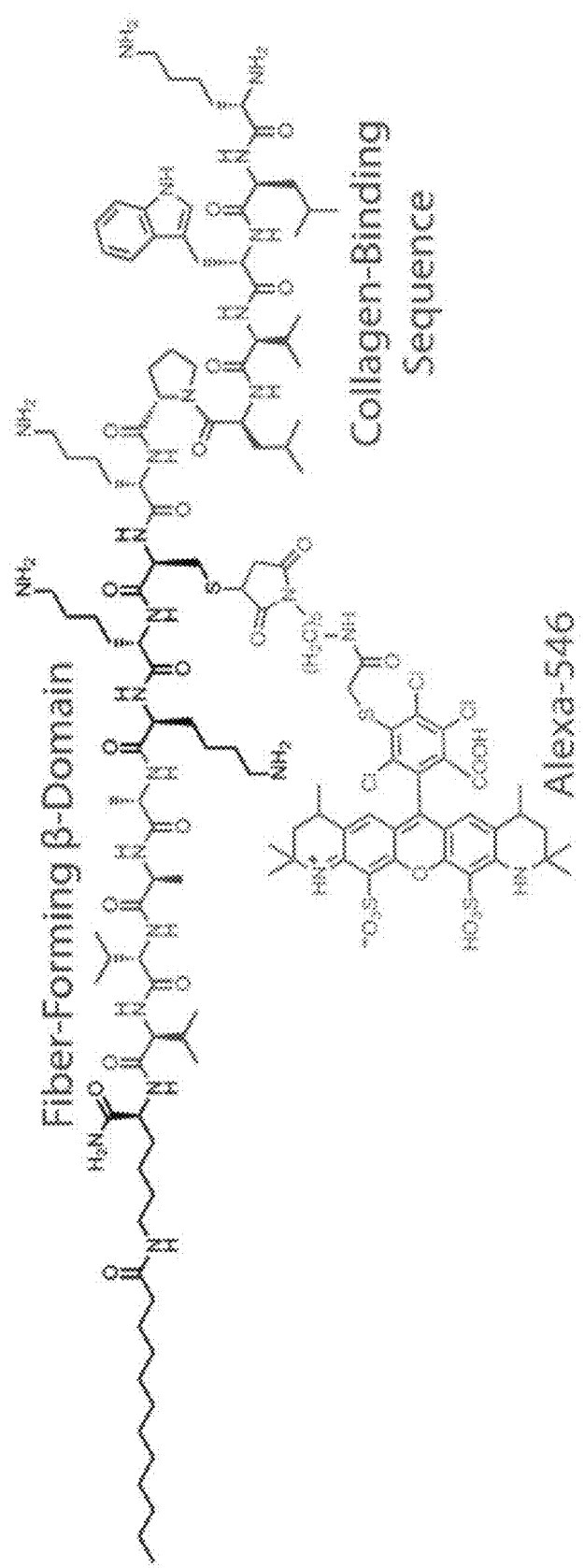
FIG. 4. Chemical structure of the fluorescently-labeled (AlexaFluor 546) collagen targeted peptide amphiphile (PA).

The rat carotid balloon injury model was used to investigate the binding specificity of the targeted nanospheres, targeted nanofibers, and non-targeted nanofibers to the injured vasculature. After injection of the fluorescently-labeled nanostructures (FIG. 4), binding to the injured artery was observed only with the targeted nanofiber (FIG. 5B). In all cases, no binding was observed to the uninjured contralateral artery. Arterial cross-sections of the respective arteries confirmed binding of the targeted nanofiber to nearly the entire luminal surface of the injured artery. Higher magnification revealed binding of the targeted nanofiber to the entire luminal surface. On the other hand, binding of the spherical nanostructures containing the targeting sequence and a diameter comparable to that of the nanofibers or of the non-targeted nanofibers was not observed on arterial cross-sections (FIG. 5B). These results indicate that the supramolecular conformation of the nanostructures has tremendous impact on binding. The experiments conducted during development of embodiments described herein to demonstrate that both the targeting sequence and a nanofiber conformation were required for binding to the injured artery in vivo.

Duration of binding of the targeted nanofiber to the injured vessel was determined by arterial harvest at various time periods. Targeted nanofiber binding to the injured vessel was observed up to 2 days after which no binding was observed. To determine the optimal dose of the targeted nanofiber for subsequent in vivo studies, animals were injected with a range of concentrations (1 to 10 mg). The lowest dose of targeted nanofiber that resulted in detectable binding to the luminal surface of the injured vessel was 1.0 mg (FIG. 5D). However, doses of 2.5 mg or greater resulted in near complete circumferential binding to the luminal surface with no subjective difference in fluorescence and binding between 2.5 mg to 10 mg. Hence, for all subsequent studies, a 5 mg dose was selected. To evaluate organ distribution of the injected nanofiber, organs were harvested at different time points, including liver, lung, kidney, spleen, heart, intestine, and brain. Fluorescence was observed within the liver and kidneys. Decreasing fluorescence was noted in the liver over time and increasing fluorescence was noted in the kidneys during the same interval. Fluorescence within the kidneys was present as early as 10 minutes and as late at 6 days. This pattern of fluorescence suggests possible initial metabolism of the fluorescently tagged nanofiber by the liver and subsequent excretion by the kidneys. There was no fluorescence detected in the brain, heart, intestine and lungs at any of the time points.

Example 4

SNO Functionalization of Targeted Nanofibers

Figure 6A:
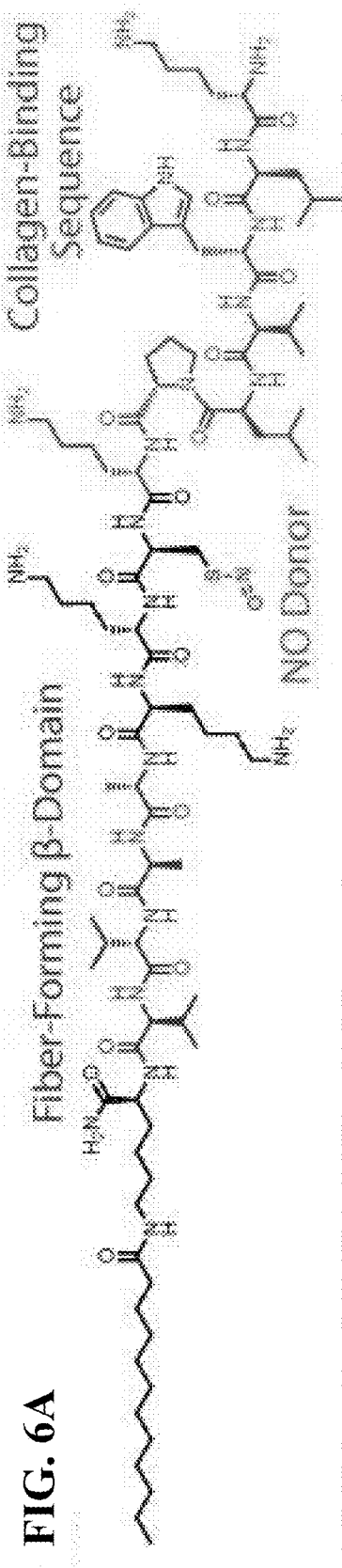
FIGS. 6A-E. Characterization of SNO-targeted nanofibers. (A) Chemical structure of S-nitrosothiol (SNO) peptide amphiphiles. (B) Cryo-transmission electron microscopy (TEM) of SNO-nanofibers. (C) Absorbance spectrum of the SNO group with addition of ascorbate and $CuCl_2$. (D) Nitric oxide (NO) release from SNO-nanofibers after the addition of ascorbate and $CuCl_2$ at 5 minutes, along with corresponding absorbance change (inset). (E) Vascular smooth muscle cell (VSMC) proliferation after exposure to SNO-nanofibers, with and without ascorbate, measured by 3H-thymidine incorporation.
Figure 6B:
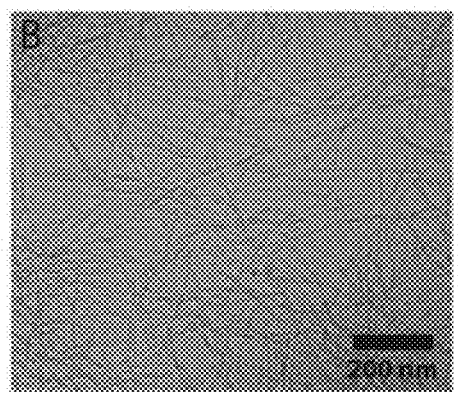
Figure 7A:
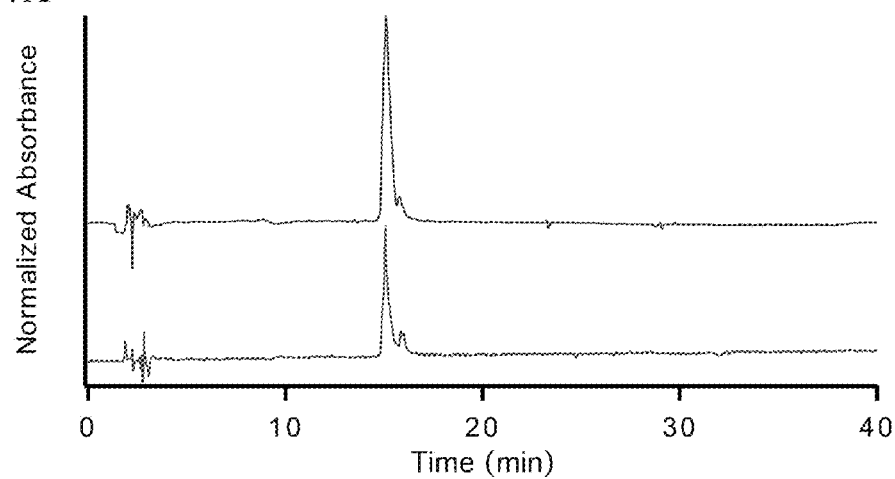
FIGS. 7A-F. S-nitrosothiol (SNO) functionalization purity and kinetics. (A) high performance liquid chromatography (HPLC) of SNO peptide amphiphiles (PA) shows one large peak for normalized absorbances at both 220 nm and 360 nm (offset for clarity) with a mass corresponding to the SNO-PA (see FIG. 8). (B) Ellman's test shows that all thiols are reacted after the addition of $NaNO_2$. (C) SNO formation corresponds to an increase in absorbance at 350 nm (D) Small angle x-ray scattering (SAXS) shows similar form factors before and after SNO formation. (E) Griess assay measurement after 24 hours shows nitrite release from the SNO-nanofiber with the addition of ascorbate and copper. (F) Nitric oxide (NO) release measured by a free radical analyzer without ascorbate (Asc) and copper (Cu) shows slow release over time.
Figure 7B:
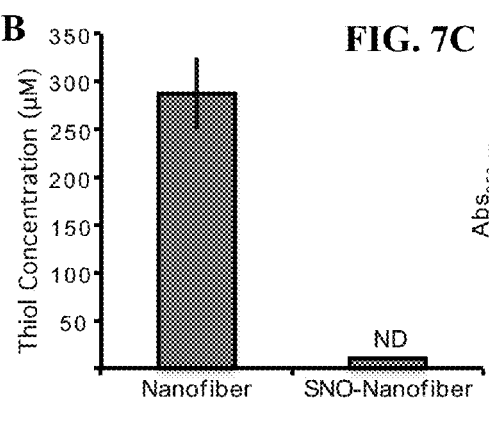
Figure 7C:
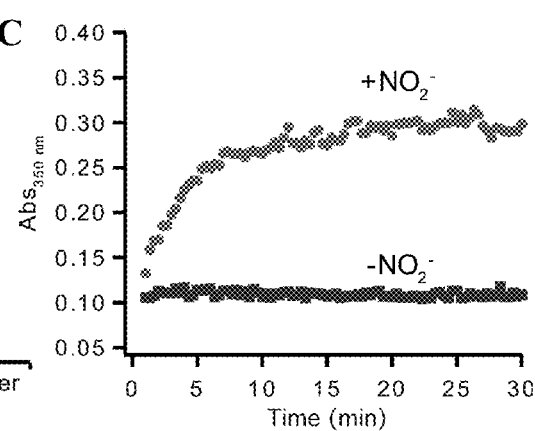
Figure 7D:
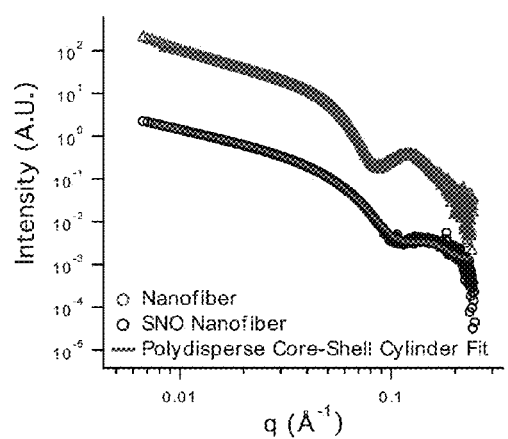
Figure 8A:
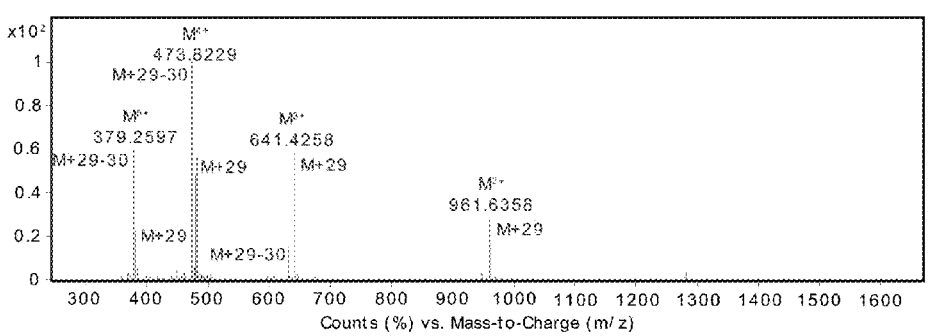
FIGS. 8A-C. Electrospray ionization (ESI) mass spectrometry (MS) of S-nitrosothiol (SNO)-targeted nanofiber. (A) Mass spectrum of the peptide amphiphile (PA) shows +2, +3, +4 and +5 peaks. At lower ionization (+2 and +3) the major peak represents the intact SNO-PA (exact mass 1921), while at higher ionization peaks (+3 to +5), the nitric oxide (NO) group is more likely to fall off as a result of ionization during MS, yielding the expected mass +29-30, or −1 relative to the unreacted targeted nanofiber. (B) Mass spectrum of unreacted nanofiber corresponds to expected peaks for an exact mass of 1892.3. (C) Deconvoluted spectrum of (A) shows the combined masses for the NO peak (M+29) and the peak after NO has fallen off during ionization, corresponding to M+29-30 (1891).
Figure 8B:
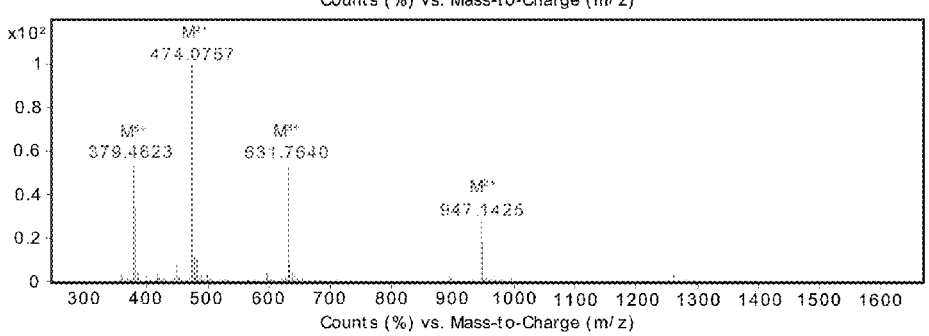
Figure 8C:
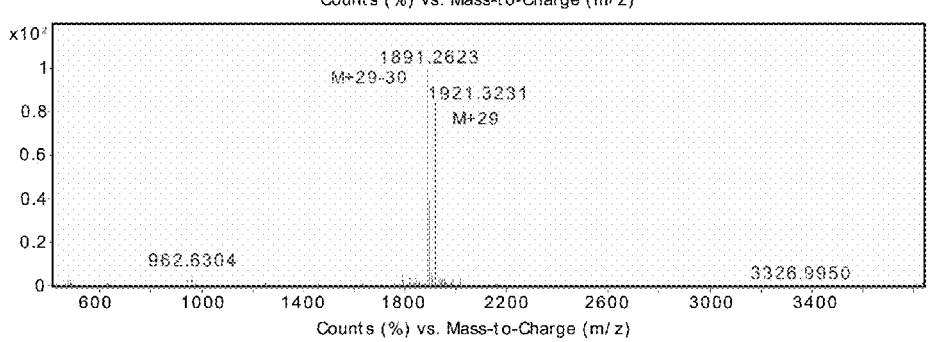

To prevent the formation of neointimal hyperplasia, the targeted nanofibers were functionalized with NO via S-nitrosylation (SNO) of the cysteine residue in the targeted nanofibers FIG. 6A). The targeted SNO-nanofiber was resolved by HPLC (FIG. 7A) and ESI-MS (FIG. 8) after incorporation of NO. Additionally, the absence of free thiols was confirmed using Ellman's reagent, which indicated full loss of free thiols after S-nitrosylation (FIG. 7B). The formation of the SNO bond leads to an absorbance peak of approximately 350 nm. This allows for detection of the SNO-nanofiber spectrophotometrically, a reaction which is complete after 15 min (FIG. 7C). Cryo-TEM showed that the SNO-functionalized PA still forms nanofibers at a neutral pH (FIG. 6B), which was confirmed by SAXS (FIG. 7D). A slight increase was observed in the radius after SNO formation, but the overall fiber structure was maintained.

Example 5

SNO Release and Bioactivity In Vitro

Figure 6C:
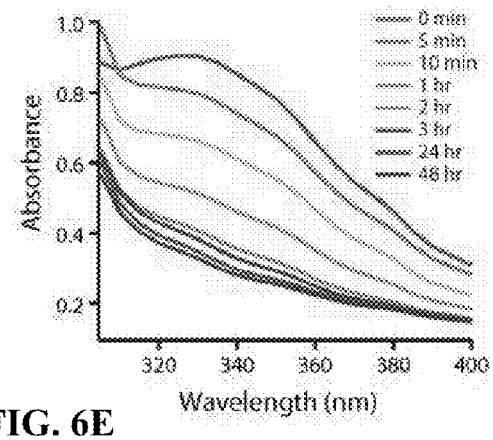
Figure 6D:
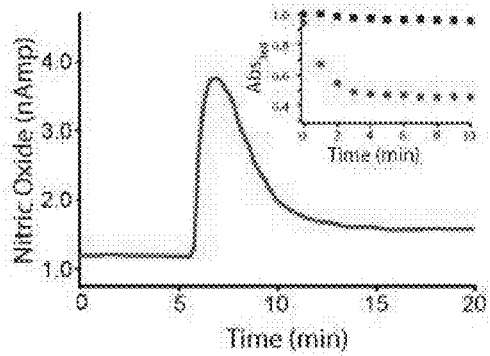
Figure 7E:
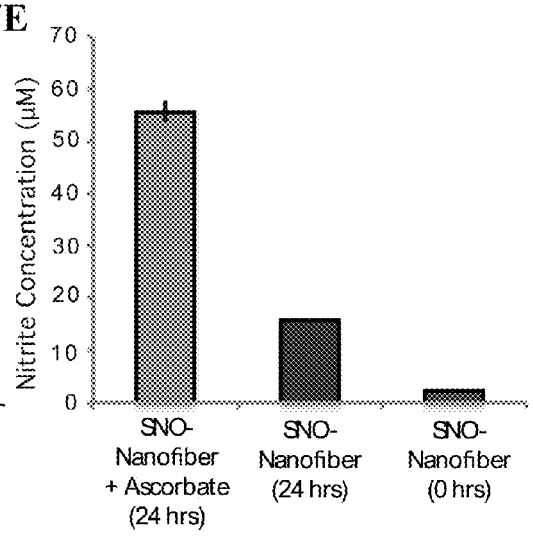
Figure 7F:
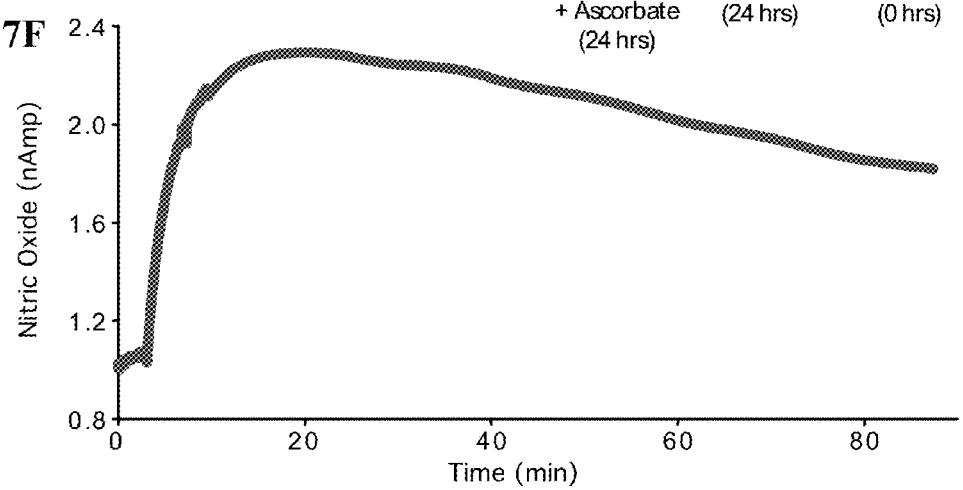

After SNO functionalization of the targeted nanofibers, NO release and cell response to this release were characterized in vitro. Though S-nitrosothiols are fairly stable in solution, they readily decompose in the presence of ascorbate and catalytic amounts of Cu. A change in absorbance was observed over time after addition of excess of ascorbate and catalytic amounts of Cu, indicating decomposition of the SNO bond of the functionalized nanofiber (FIG. 6C). In vitro, the absorbance kinetic trace showed pseudo-first order decay with an apparent $t_{1/2}$ of 49 sec. (FIG. 6D (inset)). To verify that the decomposition of the SNO bond resulted in NO release, a Griess assay was performed to quantify $NO_2^-$. Exposure of the SNO-nanofiber to ascorbate and Cu(II) resulted in over 0.9 equivalents of $NO_2^-$ in 24 hours (FIG. 7E). In PBS, pH 7.4, without ascorbate, the release was slowed significantly (FIG. 7E/F). As $NO_2^-$ is only an indirect measure of NO release, an NO electrode was used to specifically detect NO in solution. In the absence of Cu and ascorbate, NO is very slowly released in agreement with the stability of the SNO bond of the nanofiber (FIG. 7F)). However, the SNO nanofiber rapidly releases NO in the presence of cupper and ascorbate. The kinetics of NO release match the decomposition of the SNO bond followed spectrophotometrically at 368 nm (FIG. 6D (inset)).

Figure 6E:
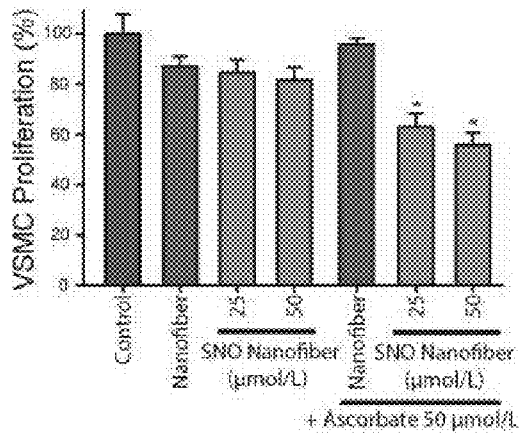

To assess the bioactivity of the NO released by the SNO-nanofiber a proliferation assay was performed using vascular smooth muscle cells (VSMC), as proliferation of VSMC is known to be inhibited by NO. Up to 50 µM, the nanofiber itself did not have an effect on VSMC proliferation (FIG. 6E). Moreover, the SNO nanofiber alone did not inhibit VSMC proliferation. However, in the presence of 50 µM ascorbate, 25 µM of the SNO-nanofiber significantly inhibited VSMC proliferation (FIG. 6E), showing that in the presence of ascorbate the SNO-nanofiber releases bioactive NO. It has previously been reported that a 5 minute exposure to NO is sufficient to inhibit neointimal hyperplasia (Havelka, G. E., et al. The Journal of surgical research 180, 35-42 (2013); herein incorporated by reference in its entirety). Moreover, after NO release in vivo, the SH moiety will most likely be regenerated back to SNO through reaction with endogenous circulating S-nitrosothiols. This will allow for continued release of NO at the site of injury as long as the nanofiber remains bound to the artery.

Example 6

Inhibition of Neointimal Hyperplasia by the Targeted SNO-Nanofiber

Figure 9A:
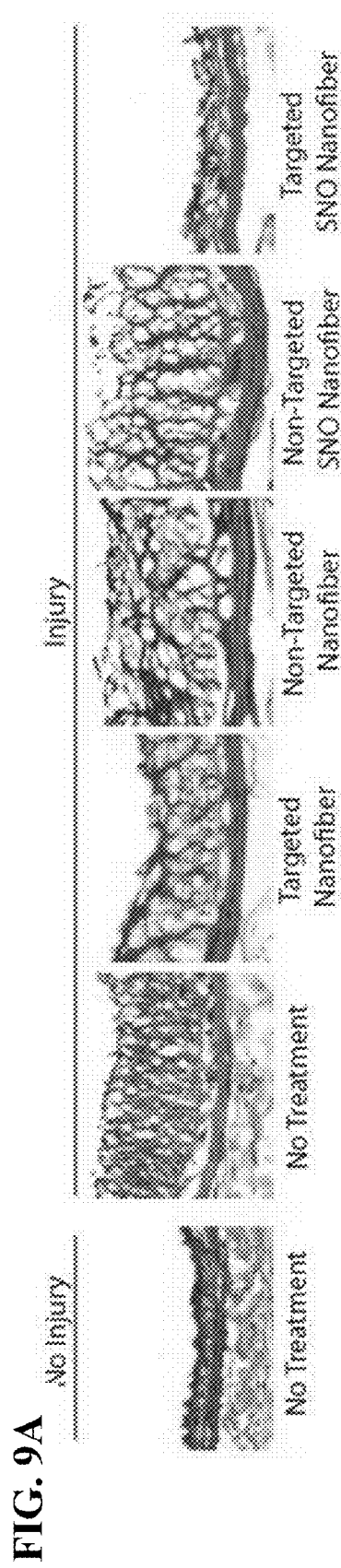
FIGS. 9A-D. Targeted SNO-nanofibers inhibit neointimal hyperplasia. (A) Arterial cross-sections of carotid arteries 2 weeks after balloon injury. (B) The targeted SNO-nanofiber inhibited intimal area by 62% versus no treatment. (C) The targeted SNO-nanofiber decreased the percent occlusion by 41% versus no treatment. (D) Immunofluorescent staining of macrophages for each treatment group.
Figure 9B:
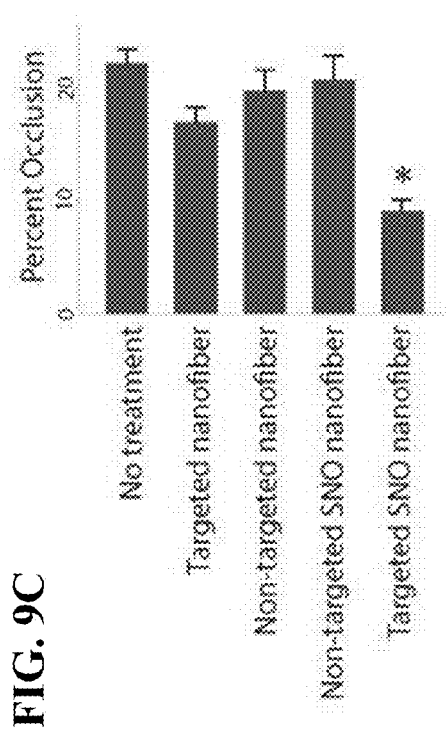
Figure 9C:
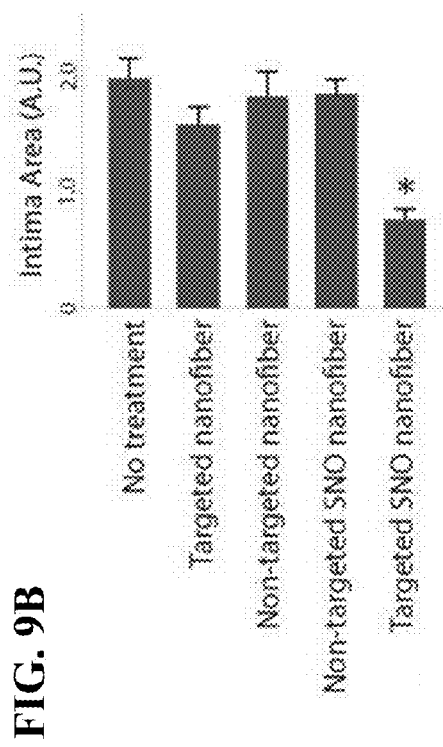
Figure 10A:
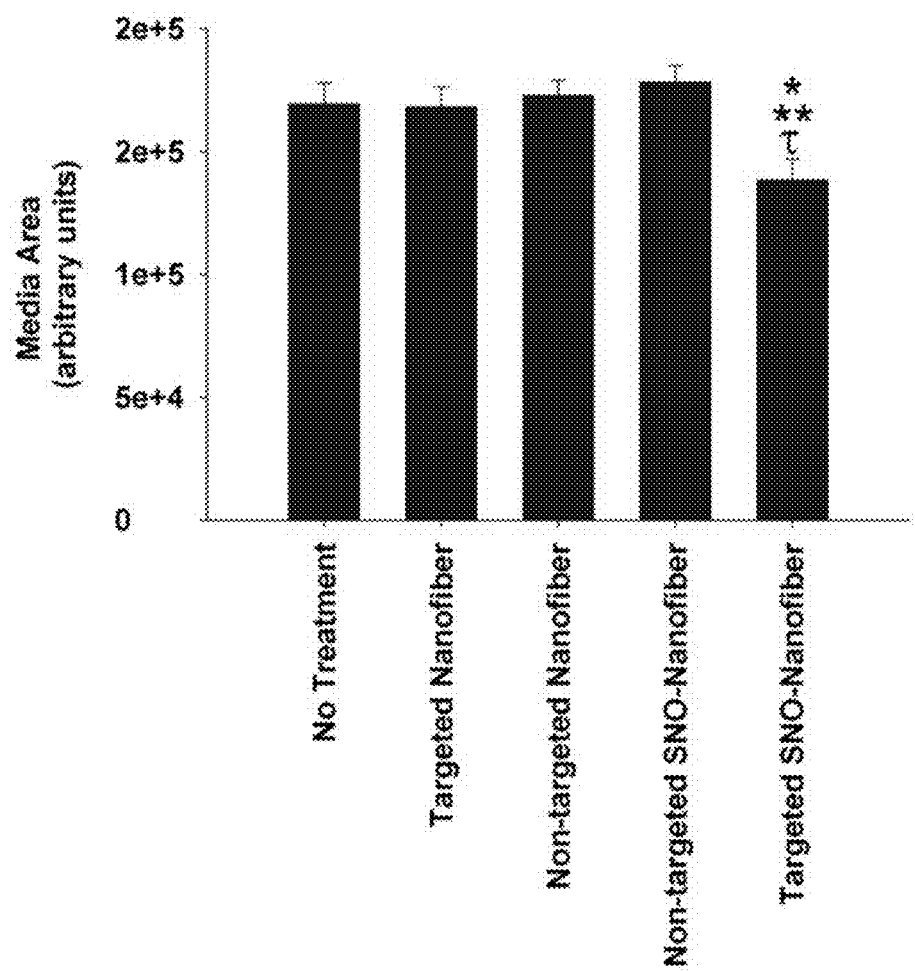
FIGS. 10A-C. Quantification of neointimal hyperplasia after arterial injury. (A) Media area decreased 20% with the targeted S-nitrosothiol (SNO)-nanofiber. (B) Lumen area increased 10% with the targeted SNO-nanofiber. (C) The intima/media (I/M) area ratio decreased 55% with the targeted SNO-nanofiber.
Figure 10B:
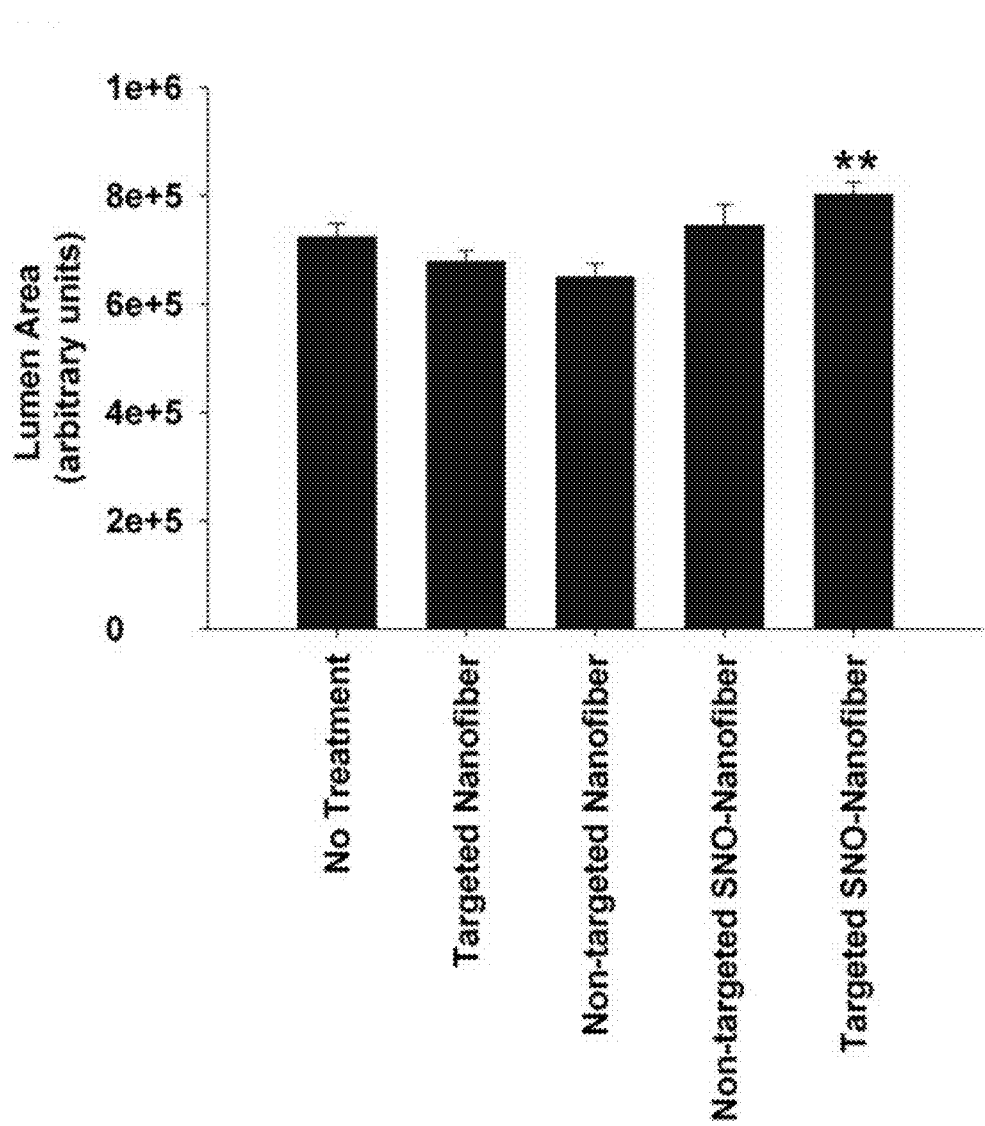
Figure 10C:
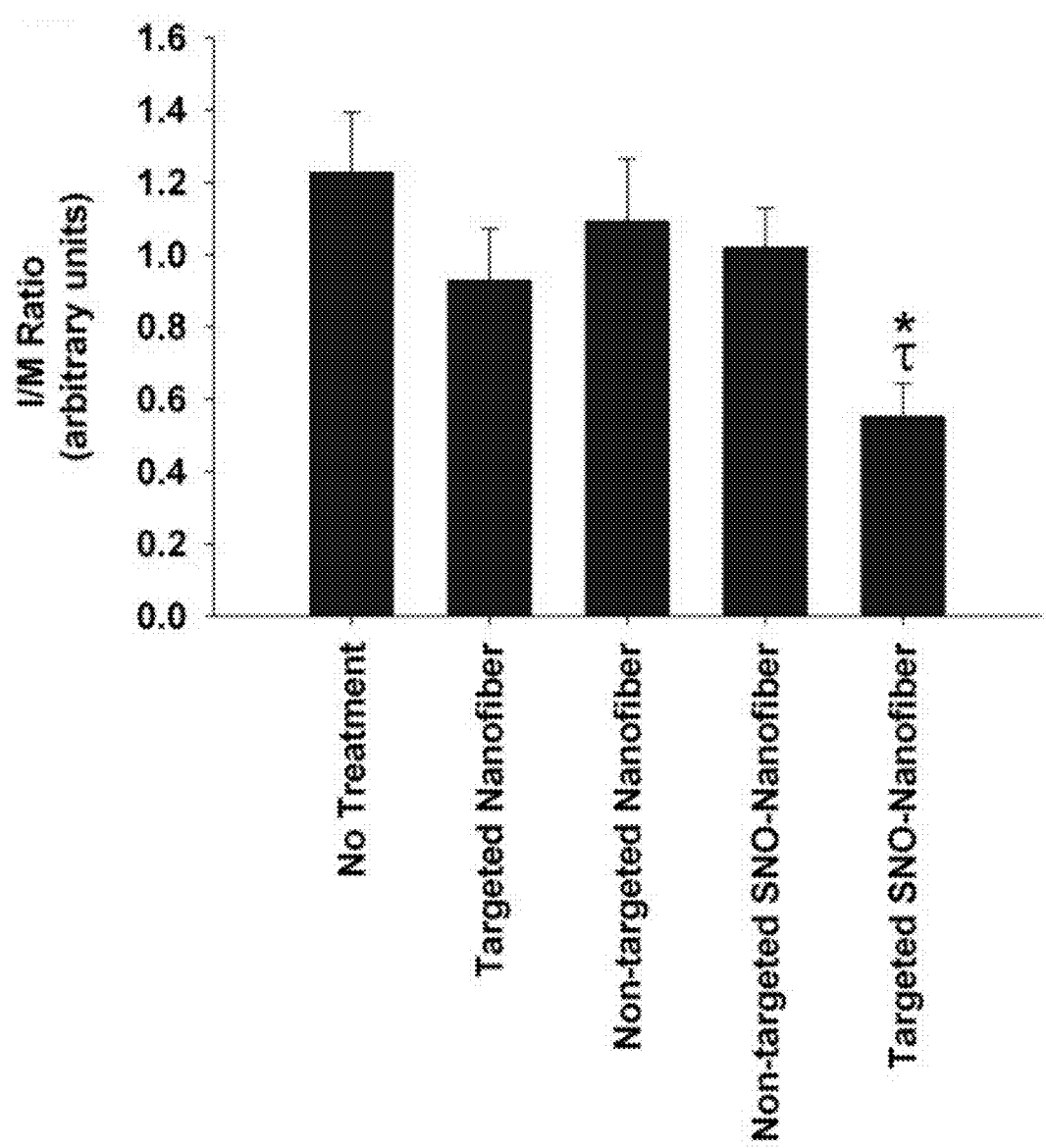
Figure 11A:
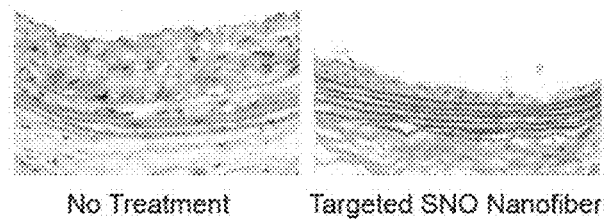
FIGS. 11A-C. Long-term durability of SNO-nanofiber inhibition of neointimal hyperplasia. (A) Representative H&E-stained arterial cross-sections of carotid arteries 7 months after balloon injury. (B) Intima to media area ratio decreased 51% with the targeted S-nitrosothiol (SNO)-nanofiber compared to control. (C) Percent occlusion decreased 45% with the targeted SNO-nanofiber compared to control.
Figure 11B:
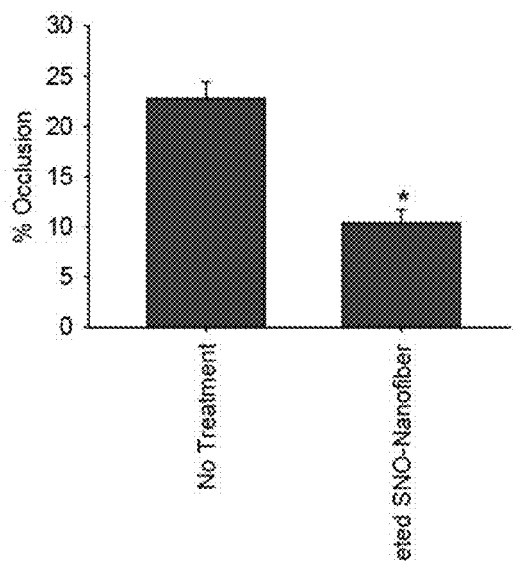
Figure 11C:
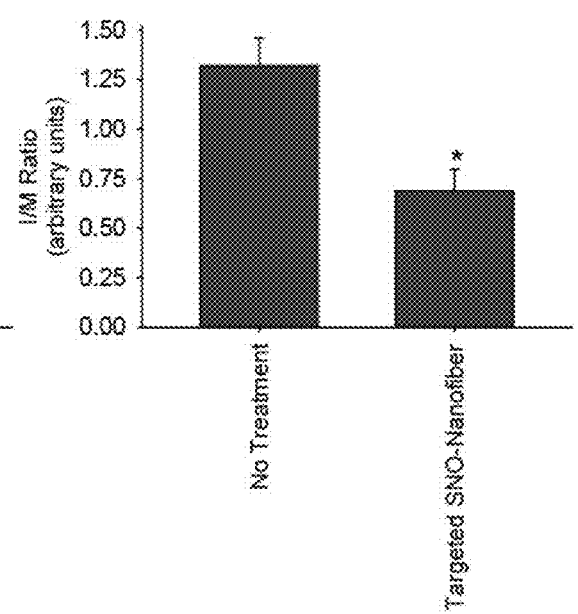
Figure 12A:
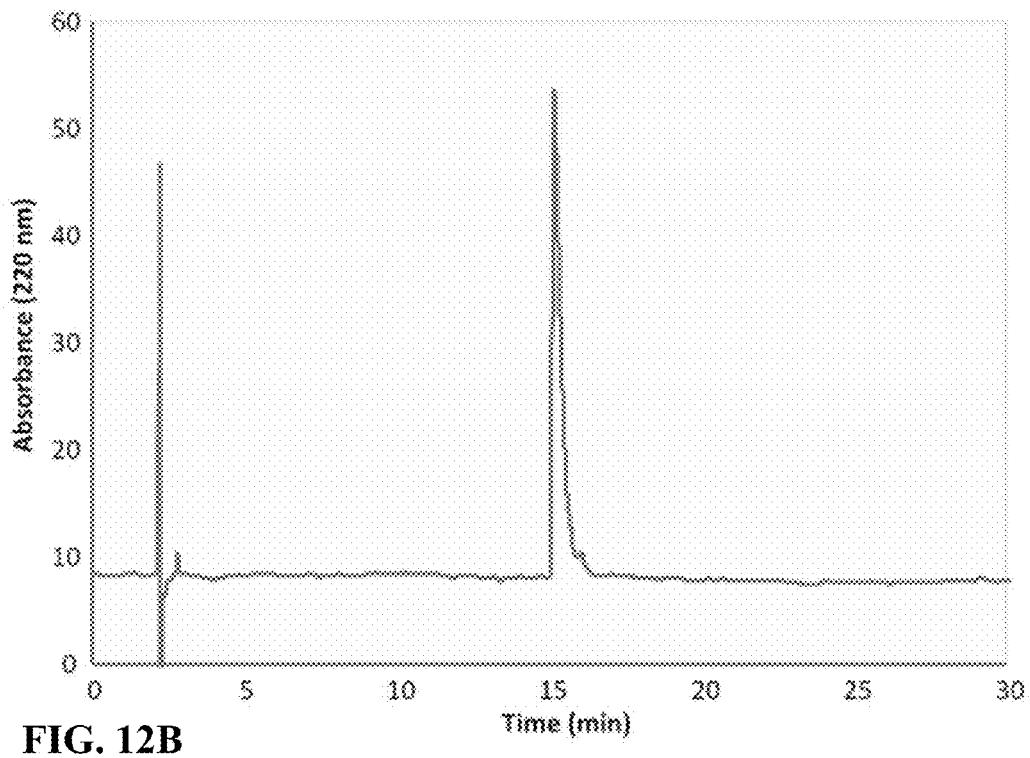
FIGS. 12A-B. Characterization of the targeted peptide amphiphile (PA). (A) High-performance liquid chromatography (HPLC) trace of the targeted PA shows 95% purity. (B) Deconvoluted electrospray ionization (ESI) mass spectrometry (MS) of the major peak from the HPLC trace.
Figure 12B:
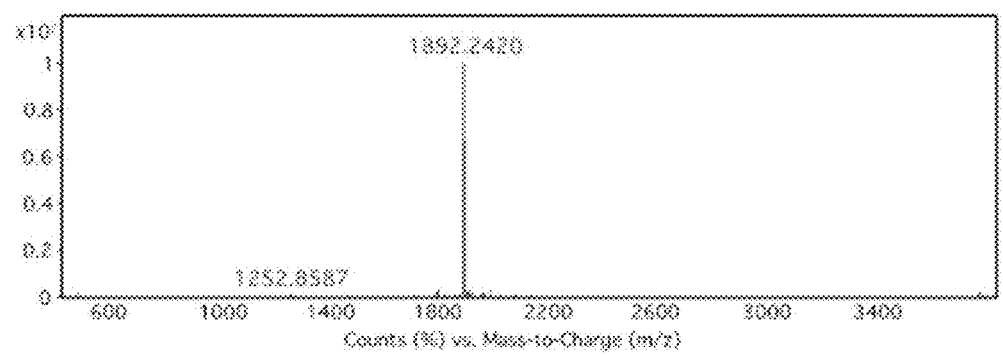

Experiments were conducted during development of embodiments described herein to determine the in vivo effect of the targeted SNO-nanofiber at inhibiting the formation of neointimal hyperplasia using the rat carotid artery balloon injury model. Evaluation of hematoxylin and eosin stained arterial cross-sections show that injury alone caused neointimal hyperplasia after 2 weeks (FIG. 9A-C). Similar levels of neointimal hyperplasia were observed in the non-targeted nanofiber, non-targeted SNO-nanofiber, and targeted nanofiber treatment groups. However, only the targeted SNO-nanofiber inhibited the development of neointimal hyperplasia upon evaluation of multiple metrics (FIG. 0A-C). There was a 62% decrease in neointimal area, and a 41% reduction in percent occlusion in the targeted SNO-nanofiber group compared to injury alone (FIG. 9B-C). The targeted SNO-nanofiber also caused a 20% decrease in the medial area, 55% decrease in the I/M area ratio, and 10% increase in lumen area compared to injury alone (FIG. 10). The inhibition of neointimal hyperplasia was durable. The targeted SNO-nanofiber continued to inhibit neointimal hyperplasia up to 7 months following arterial balloon injury, causing a 51% decrease in I/M area ratio and a 45% reduction in percent occlusion compared to injury alone (FIG. 11). With respect to inflammation, no subjective difference was observed in macrophage infiltration between the 5 different treatment groups on immunofluorescent staining of arteries harvested at 2 weeks.

Another important observation is that the targeted SNO-nanofiber significantly inhibited neointimal hyperplasia compared to both the non-targeted SNO-nanofiber and the targeted nanofiber without NO functionalization. Compared to the non-targeted SNO-nanofiber, the targeted SNO-nanofiber inhibited intimal area by 58%, medial area by 22%, I/M area ratio by 46%, and percent occlusion by 56% (FIGS. 9 and 10). Compared to the targeted nanofiber without NO functionalization, the targeted SNO-nanofiber inhibited intimal area by 52%, medial area by 18%, and percent occlusion by 46%, and increased lumen area by 18% (p=0.012) (FIGS. 9 and 10). No differences were observed in the medial area, lumen area, and I/M area ratio between the no treatment, targeted nanofiber, and non-targeted SNO-nanofiber.

Together, these data indicate that the integration of the collagen-binding sequence for targeting and the chemistry for NO delivery into a filamentous supramolecular vehicle are essential for a therapeutic effect.

Figure 9D:
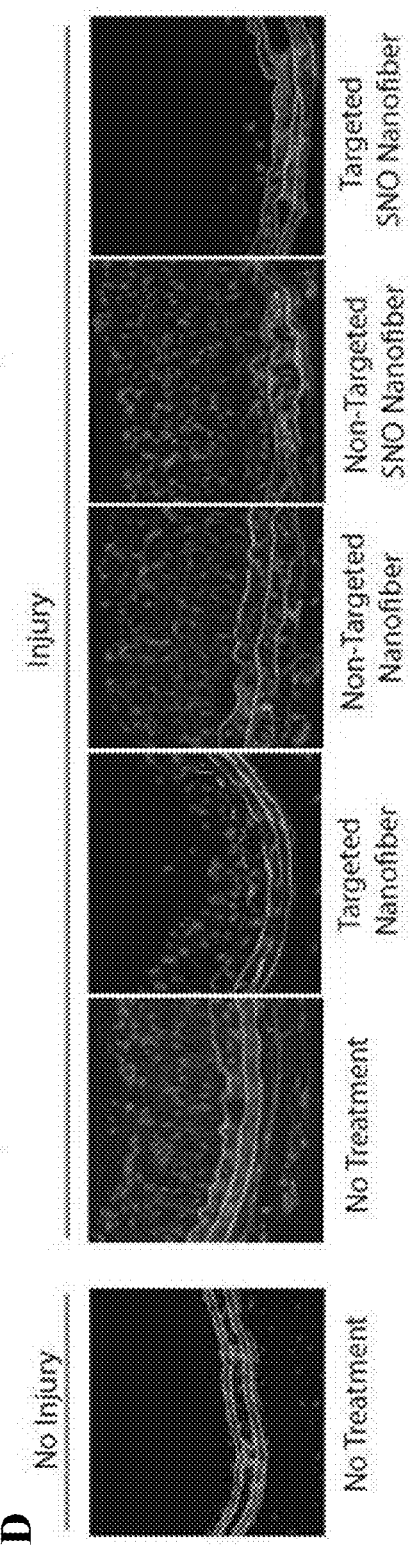

Experiments were conducted during development of embodiments described herein to evaluate whether these nanofiber constructs induced inflammation in the vasculature. Evaluation of the arterial section using immunofluorescent staining for macrophages revealed no differences between the five treatment groups at 2 weeks (FIG. 9D).

REFERENCES

1. Clowes A W, Reidy M A, Clowes M M. Kinetics of cellular proliferation after arterial injury. I. Smooth muscle growth in the absence of endothelium. Laboratory investigation; a journal of technical methods and pathology. 1983; 49:327-333
2. Clowes A W, Clowes M M. Kinetics of cellular proliferation after arterial injury. II. Inhibition of smooth muscle growth by heparin. Laboratory investigation; a journal of technical methods and pathology. 1985; 52:611-616
3. Clowes A W, Clowes M M, Reidy M A. Kinetics of cellular proliferation after arterial injury. III. Endothelial and smooth muscle growth in chronically denuded vessels. Laboratory investigation; a journal of technical methods and pathology. 1986; 54:295-303
4. Radomski M W, Palmer R M, Moncada S. Endogenous nitric oxide inhibits human platelet adhesion to vascular endothelium. Lancet. 1987; 2:1057-1058
5. Garg U C, Hassid A. Nitric oxide-generating vasodilators and 8-bromo-cyclic guanosine monophosphate inhibit mitogenesis and proliferation of cultured rat vascular smooth muscle cells. J. Clin. Invest. 1989; 83:1774
6. Kubes P, Suzuki M, Granger D N. Nitric oxide: An endogenous modulator of leukocyte adhesion. Proceedings of the National Academy of Sciences. 1991; 88:4651-4655
7. Furchgott R F, Zawadzki J V. The obligatory role of endothelial cells in the relaxation of arterial smooth muscle by acetylcholine. Nature. 1980; 288:373-376
8. Davies M G, Kim J H, Dalen H, Makhoul R G, Svendsen E, Hagen P O. Reduction of experimental vein graft intimal hyperplasia and preservation of nitric oxide-mediated relaxation by the nitric oxide precursor 1-arginine. Surgery. 1994; 116:557-568
9. Guo J P, Panday M M, Consigny P M, Lefer A M. Mechanisms of vascular preservation by a novel no donor following rat carotid artery intimal injury. The American journal of physiology. 1995; 269:H1122-1131
10. Lee J S, Adrie C, Jacob H J, Roberts J D, Jr., Zapol W M, Bloch K D. Chronic inhalation of nitric oxide inhibits neointimal formation after balloon-induced arterial injury. Circulation research. 1996; 78:337-342
11. Napoli C, Cirino G, Del Soldato P, Sorrentino R, Sica V, Condorelli M, Pinto A, Ignarro L J. Effects of nitric oxide-releasing aspirin versus aspirin on restenosis in hypercholesterolemic mice. Proceedings of the National Academy of Sciences of the United States of America. 2001; 98:2860-2864
12. Lablanche J M, Grollier G, Lusson J R, Bassand J P, Drobinski G, Bertrand B, Battaglia S, Desveaux B, Juilliere Y, Juliard J M, Metzger J P, Coste P, Quiret J C, Dubois-Rande J L, Crochet P D, Letac B, Boschat J, Virot P, Finet G, Le Breton H, Livarek B, Leclercq F, Beard T, Giraud T, Bertrand M E, et al. Effect of the direct nitric oxide donors linsidomine and molsidomine on angiographic restenosis after coronary balloon angioplasty. The accord study. Angioplastic coronaire corvasal diltiazem. Circulation. 1997; 95:83-89
13. von der Leyen H E, Gibbons G H, Morishita R, Lewis N P, Zhang L, Nakajima M, Kaneda Y, Cooke J P, Dzau V J. Gene therapy inhibiting neointimal vascular lesion: In vivo transfer of endothelial cell nitric oxide synthase gene. Proceedings of the National Academy of Sciences of the United States of America. 1995; 92:1137-1141
14. Varenne O, Pislaru S, Gillijns H, Van Pelt N, Gerard R D, Zoldhelyi P, Van de Werf F, Collen D, Janssens S P. Local adenovirus-mediated transfer of human endothelial nitric oxide synthase reduces luminal narrowing after coronary angioplasty in pigs. Circulation. 1998; 98:919-926
15. Shears L L, 2nd, Kibbe M R, Murdock A D, Billiar T R, Lizonova A, Kovesdi I, Watkins S C, Tzeng E. Efficient inhibition of intimal hyperplasia by adenovirus-mediated inducible nitric oxide synthase gene transfer to rats and pigs in vivo. Journal of the American College of Surgeons. 1998; 187:295-306
16. Schwarzacher S P, Lim T T, Wang B, Kernoff R S, Niebauer J, Cooke J P, Yeung A C. Local intramural delivery of 1-arginine enhances nitric oxide generation and inhibits lesion formation after balloon angioplasty. Circulation. 1997; 95:1863-1869
17. Marks D S, Vita J A, Folts J D, Keaney J F, Jr., Welch G N, Loscalzo J Inhibition of neointimal proliferation in rabbits after vascular injury by a single treatment with a protein adduct of nitric oxide. The Journal of clinical investigation. 1995; 96:2630-2638
18. Fulton G J, Davies M G, Barber L, Gray J L, Svendsen E, Hagen P O. Local effects of nitric oxide supplementation and suppression in the development of intimal hyperplasia in experimental vein grafts. European journal of vascular and endovascular surgery: the official journal of the European Society for Vascular Surgery. 1998; 15:279-289
19. Pearce C G, Najjar S F, Kapadia M R, Murar J, Eng J, Lyle B, Aalami O O, Jiang Q, Hrabie J A, Saavedra J E, Keefer L K, Kibbe M R. Beneficial effect of a short-acting no donor for the prevention of neointimal hyperplasia. Free radical biology & medicine. 2008; 44:73-81
20. Ziche M, Morbidelli L, Masini E, Amerini S, Granger H J, Maggi Cea, Geppetti P, Ledda F. Nitric oxide mediates angiogenesis in vivo and endothelial cell growth and migration in vitro promoted by substance p. J. Clin. Invest. 1994; 94:2036
21. Keefer L K. Progress toward clinical application of the nitric oxide-releasing diazeniumdiolates. Annual review of pharmacology and toxicology. 2003; 43:585-607
22. Hrkach J, Von Hoff D, Ali M M, Andrianova E, Auer J, Campbell T, De Witt D, Figa M, Figueiredo M, Horhota A, Low S, McDonnell K, Peeke E, Retnarajan B, Sabnis A, Schnipper E, Song J J, Song Y H, Summa J, Tompsett D, Troiano G, Van Geen Hoven T, Wright J, LoRusso P, Kantoff P W, Bander N H, Sweeney C, Farokhzad O C, Langer R, Zale S. Preclinical development and clinical translation of a psma-targeted docetaxel nanoparticle with a differentiated pharmacological profile. Science Translational Medicine. 2012; 4:12839-12839
23. Farokhzad O C, Jon S, Khademhosseini A, Tran T-N T, LaVan D A, Langer R. Nanoparticle-aptamer bioconjugates a new approach for targeting prostate cancer cells. Cancer Research. 2004; 64:7668-7672
24. Qian X, Peng X-H, Ansari D O, Yin-Goen Q, Chen G Z, Shin D M, Yang L, Young A N, Wang M D, Nie S. In vivo tumor targeting and spectroscopic detection with surface-enhanced raman nanoparticle tags. Nat Biotechnol. 2007; 26:83-90
25. Davis M E, Zuckerman J E, Choi C H J, Seligson D, Tolcher A, Alabi C A, Yen Y, Heidel J D, Ribas A. Evidence of rnai in humans from systemically administered sirna via targeted nanoparticles. Nature. 2010; 464: 1067-1070
26. Choi C H J, Alabi C A, Webster P, Davis M E. Mechanism of active targeting in solid tumors with transferrin-containing gold nanoparticles. Proceedings of the National Academy of Sciences. 2010; 107:1235-1240
27. Vance D, Martin J, Patke S, Kane R S. The design of polyvalent scaffolds for targeted delivery. Advanced Drug Delivery Reviews. 2009; 61:931-939
28. Chan J M, Zhang L, Tong R, Ghosh D, Gao W, Liao G, Yuet K P, Gray D, Rhee J W, Cheng J, Golomb G, Libby P, Langer R, Farokhzad O C. Spatiotemporal controlled delivery of nanoparticles to injured vasculature. Proceedings of the National Academy of Sciences. 2010; 107: 2213-2218
29. Geng Y, Dalhaimer P, Cai S, Tsai R, Tewari M, Minko T, Discher D E. Shape effects of filaments versus spherical particles in flow and drug delivery. Nature Nanotechnology. 2007; 2:249-255
30. Decuzzi P, Pasqualini R, Arap W, Ferrari M. Intravascular delivery of particulate systems: Does geometry really matter? Pharm Res. 2008; 26:235-243
31. Doshi N, Prabhakarpandian B, Rea-Ramsey A, Pant K, Sundaram S, Mitragotri S. Flow and adhesion of drug carriers in blood vessels depend on their shape: A study using model synthetic microvascular networks. Journal of Controlled Release. 2010; 146:196-200
32. LeBleu V S, MacDonald B, Kalluri R. Structure and function of basement membranes. Experimental Biology and Medicine. 2007; 232:1121-1129
33. Chan J M, Rhee J W, Drum C L, Bronson R T, Golomb G, Langer R, Farokhzad O C. In vivo prevention of arterial restenosis with paclitaxel-encapsulated targeted lipid-polymeric nanoparticles. Proceedings of the National Academy of Sciences. 2011; 108:19347-19352
34. Hrabie J A, Keefer L K. Chemistry of the nitric oxide-releasing diazeniumdiolate ("nitrosohydroxylamine") functional group and its oxygen-substituted derivatives. Chemical reviews. 2002; 102:1135-1154
35. Stamler J S. S-nitrosothiols and the bioregulatory actions of nitrogen oxides through reactions with thiol groups. Current topics in microbiology and immunology. 1995; 196:19-36
36. Hartgerink J D, Beniash E, Stupp S I. Self-assembly and mineralization of peptide-amphiphile nanofibers. Science. 2001; 294:1684-1688
37. Cui H, Webber M J, Stupp S I. Self-assembly of peptide amphiphiles: From molecules to nanostructures to biomaterials. Biopolymers. 2010; 94:1-18
38. Matson J B, Stupp S I. Self-assembling peptide scaffolds for regenerative medicine. Chemical Communications. 2012; 48:26-33
39. Soukasene S, Toft D J, Moyer T J, Lu H, Lee H-K, Standley S M, Cryns V L, Stupp S I. Antitumor activity of peptide amphiphile nanofiber-encapsulated camptothecin. ACS Nano. 2011; 5:9113-9121
40. Cui H, Muraoka T, Cheetham A G, Stupp S I. Self-assembly of giant peptide nanobelts. Nano Lett. 2009; 9:945-951
41. Muraoka T, Koh C-Y, Cui H, Stupp S I. Light-triggered bioactivity in three dimensions. Angew. Chem. Int. Ed. 2009; 48:5946-5949
42. Pashuck E T, Stupp S I. Direct observation of morphological tranformation from twisted ribbons into helical ribbons. J. Am. Chem. Soc. 2010; 132:8819-8821
43. Kapadia M R, Chow L W, Tsihlis N D, Ahanchi S S, Eng J W, Murar J, Martinez J, Popowich D A, Jiang Q, Hrabie J A, Saavedra J E, Keefer L K, Hulvat J F, Stupp S I, Kibbe M R. Nitric oxide and nanotechnology: A novel approach to inhibit neointimal hyperplasia. Journal of vascular surgery. 2008; 47:173-182
44. Matson J B, Webber M J, Tamboli V K, Weber B, Stupp S I. A peptide-based material for therapeutic carbon monoxide delivery. Soft matter. 2012; 8:2689-2692
45. Soukasene S, Toft D J, Moyer T J, Lu H, Lee H K, Standley S M, Cryns V L, Stupp S I. Antitumor activity of peptide amphiphile nanofiber-encapsulated camptothecin. ACS Nano. 2011; 5:9113-9121
46. Toft D J, Moyer T J, Standley S M, Ruff Y, Ugolkov A, Stupp S I, Cryns V L. Coassembled cytotoxic and pegylated peptide amphiphiles form filamentous nanostructures with potent antitumor activity in models of breast cancer. ACS Nano. 2012; 6:7956-7965
47. Mathews W R, Kerr S W. Biological activity of s-nitrosothiols: The role of nitric oxide. Journal of Pharmacology and Experimental Therapeutics. 1993; 267:1529-1537
48. Vavra A K, Havelka G E, Martinez J, Lee V R, Fu B, Jiang Q, Keefer L K, Kibbe M R. Insights into the effect of nitric oxide and its metabolites nitrite and nitrate at inhibiting neointimal hyperplasia. Nitric oxide: biology and chemistry/official journal of the Nitric Oxide Society. 2011; 25:22-30
49. McNamara D B, Bedi B, Aurora H, Tena L, Ignarro L J, Kadowitz P J, Akers D L. L-arginine inhibits balloon catheter-induced intimal hyperplasia. Biochemical and biophysical research communications. 1993; 193:291-296
50. Havelka G E, Moreira E S, Rodriguez M P, Tsihlis N D, Wang Z, Martinez J, Hrabie J A, Keefer L K, Kibbe M R. Nitric oxide delivery a permeable balloon catheter inhibits neointimal growth after arterial injury. Journal of Surgical Research. March 2013; 180(1):35-42.

All publications and patents listed above and/or provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A peptide amphiphile comprising:
   (a) a hydrophobic non-peptidic segment;
   (b) a β-sheet-forming peptide segment;
   (c) a charged peptide segment;
   (d) a targeting moiety, wherein the targeting moiety comprises a binding sequence for collagen IV and comprises a 6 amino acid segment with at least 50% sequence identity with KLVWLPK (SEQ ID NO: 2); and
   (e) a therapeutic agent;
   wherein the hydrophobic non-peptidic segment is covalently attached to the N-terminus of the β-sheet-forming peptide segment;
   wherein the C-terminus of the β-sheet-forming peptide segment is covalently attached to the N-terminus of the charged peptide segment; and
   wherein the C-terminus of the charged peptide segment is covalently attached to the N-terminus of the targeting moiety.

2. The peptide amphiphile of claim 1, wherein the hydrophobic non-peptidic segment comprises an acyl chain.

3. The peptide amphiphile of claim 2, wherein the acyl chain comprises C6-C20.

4. The peptide amphiphile of claim 3, wherein the acyl chain comprises lauric acid.

5. The peptide amphiphile of claim 1, wherein the β-sheet-forming peptide segment comprises AAVV (SEQ ID NO: 3).

6. The peptide amphiphile of claim 1, wherein the charged peptide segment comprises a plurality of Lys (K), Arg (R), Glu (E) and/or Asp (D) residues.

7. The peptide amphiphile of claim 1, wherein the targeting moiety comprises a binding sequence for a target protein.

8. The peptide amphiphile of claim 1, wherein the binding sequence comprises KLVWLPK (SEQ ID NO: 2).

9. The peptide amphiphile of claim 1, wherein the therapeutic agent is covalently linked to a portion of (b)-(d).

10. The peptide amphiphile of claim 9, wherein the therapeutic agent is nitric oxide (NO).

11. The peptide amphiphile of claim 10, wherein the NO is covalently linked to a portion of (b)-(d) as a nitroso group.

12. The peptide amphiphile of claim 11, wherein the nitroso group is attached via nitrosylation of a cysteine residue.

13. The peptide amphiphile of claim 1, comprising an S-nitrosylated cysteine residue.

14. A self-assembled nanofiber formed of the peptide amphiphiles of claim 1.

15. A method of treating or preventing cardiovascular restenosis comprising administering to a subject the self-assembled nanofiber of claim 14.

16. The peptide amphiphile of claim 7, wherein the target protein is selected from the list consisting of elastin, laminin, fibroinectin, collagen I, collagen III, collagen IV, and collagen V.

17. The peptide amphiphile of claim 16, wherein the target protein is collagen IV.

18. A peptide amphiphile comprising:
(a) a hydrophobic non-peptidic segment comprising a $(CH_2)_{12}$ tail;
(b) a peptide portion with at least 50% sequence identity with $KLVWLPKCK_2A_2V_2K$ (SEQ ID NO: 1); and
(c) a therapeutic agent;
wherein the hydrophobic non-peptidic segment is covalently attached to the N-terminus of the peptide portion.

19. The peptide amphiphile of claim 18, comprising $KLVWLPKCK_2A_2V_2K$—$(CH_2)_{12}$ (SEQ ID NO: 1) tail.

20. The peptide amphiphile of claim 18, comprising an S-nitrosylated cysteine residue.

21. A self-assembled nanofiber formed of the peptide amphiphiles of claim 18.

\* \* \* \* \*